(12) United States Patent
Hatzis et al.

(10) Patent No.: US 7,711,494 B2
(45) Date of Patent: May 4, 2010

(54) METHOD OF MEASURING RESIDUAL CANCER AND PREDICTING PATIENT SURVIVAL

(75) Inventors: Christos Hatzis, Melrose, MA (US); W. Fraser Symmans, Houston, TX (US); Lajos Pusztai, Pearland, TX (US)

(73) Assignees: Board of Regents, The University of Texas System, Austin, TX (US); Nuvera Biosciences, Inc., Woburn, MA (US)

( * ) Notice: Subject to any disclaimer, the term of this patent is extended or adjusted under 35 U.S.C. 154(b) by 392 days.

(21) Appl. No.: 11/786,980

(22) Filed: Apr. 13, 2007

(65) Prior Publication Data

US 2007/0248948 A1    Oct. 25, 2007

Related U.S. Application Data

(60) Provisional application No. 60/792,245, filed on Apr. 14, 2006.

(51) Int. Cl.
*C12Q 1/00* (2006.01)
*G06F 19/00* (2006.01)

(52) U.S. Cl. ............................. 702/19; 435/4; 703/11

(58) Field of Classification Search ...................... None
See application file for complete search history.

(56) References Cited

OTHER PUBLICATIONS

Wazer et al. Int. Journal of Radiation Oncology, 38 (2), 1997; see Abstract on p. 291.*
Escobar et al., "Prognostic Significance of Residual Breast Disease and Axillary Node Involvement for Patients Who Had Primary Induction Chemotherapy for Advanced Breast Cancer", *Ann. Surg. Oncol.*, 13(6):783-787 (2006).
Hatzis et al., "Genomic predictor of benefit from endocrine therapy also predicts response to chemotherapy", *Breast Cancer Res. Treat.*, 29th *Ann. San Antonio Breast Cancer Symposium*, #3030, Dec. 14-17, 2006, (Abstract Only).
Klauber-Demore et al., "Size of Residual Lymph Node Metastasis After Neoadjuvant Chemotherapy in Locally Advanced Breast Cancer Patients Is Prognostic", Ann. Surg. Oncol., 13(5):685-691 (2006).
Rajan et al., "Change in Tumor Cellularity of Breast Carcinoma after Neoadjuvant Chemotherapy As a Variable in the Pathologic Assessment of Response", Cancer, 100(7):1365-1373 (2004).
Altman et al., "What do we mean by validating a prognostic model?", *Stat. Med.*, 19:453-473 (2000).
Feldman et al., "Pathological assessment of response to induction chemotherapy in breast cancer", *Cancer Res.*, 46:2578-2581 (1986).
Green et al., "Weekly paclitaxel improves pathologic complete remission in operable breast cancer when compared with paclitaxel once every 3 weeks", *J. Clin. Oncol.*, 23(25):5983-5992 (2005).
Harrell, F.E., Jr., "Regression modeling strategies: with applications to linear models, logistic regression, and survival analysis", New York: Springer-Verlag (2001).
Hortobagyi et al., "Management of stage III breast cancer with primary chemotherapy, surgery, and radiation therapy", *Cancer*, 62(12):2507-2516 (1988).
Justice et al., "Assessing the generalizability of prognostic information", *Ann. Intern. Med.*, 130:515-524 (1999).
Kattan, M.W., "Judging new markers by their ability to improve predictive accuracy", *J. Natl. Cancer* Inst., 95(9):634-635 (2003).
Kurosumi, M., "Significance of histopathological evaluatin in primary therapy for breast cancer—recent trends in primary modality with pathological complete response (pCR) as endpoint" *Breast Cancer*, 11(2):139-147 (2004).
Sataloff et al., "Pathologic response to induction chemotherapy in locally advanced carcinoma of the breast: a determinant of outcome", *J. Am. Coll. Surg.*, 180:297-306 (1995).
Schumacher et al., "Resampling and cross-validation techniques: a tool to reduce bias caused by model building?", *Statistics Med.*, 16:2813-2827 (1997).
Simon, R., "Roadmap for developing and validating therapeutically relevant genomic classifiers", *J. Clin. Oncol.*, 23(29):7332-7341 (2005).

* cited by examiner

*Primary Examiner*—Michael Borin
(74) *Attorney, Agent, or Firm*—Mintz, Levin, Cohn, Ferris, Glovsky and Popeo, P.C.; David E. Johnson

(57) ABSTRACT

Disclosed is a method for determining survival and relapse of a patient undergoing therapy for a tumor by determining a residual cancer burden index based on the bidimensional diameters of a primary tumor bed of said tumor in a resection specimen, the proportion of the primary tumor bed area that contains invasive carcinoma, the number of regional lymph nodes containing metastatic carcinoma, the diameter of the largest metastasis in an regional lymph node; and the fractional reduction in lymph node size with each added positive lymph node.

14 Claims, 32 Drawing Sheets

| VARIABLE | HAZARD RATIO (95% CI) | P VALUE |
|---|---|---|
| PRIMARY TUMOR BED DIMENSIONS ($\sqrt{d_1 d_2}$) | 1.24 (1.04-1.48) | 0.02 |
| CELLULARITY FRACTION OF INVASIVE CANCER ($f_{inv}$) | 7.37 (2.16-25.1) | 0.001 |
| SIZE OF LARGEST METASTASIS ($d_{met}$) | 1.17 (0.99-1.38) | 0.06 |
| NUMBER OF POSITIVE LYMPH NODES ($LN$) | 1.11 (1.04-1.19) | 0.002 |

Fig. 1

METHOD OF MEASURING RESIDUAL CANCER AND PREDICTING PATIENT SURVIVAL

RELATED APPLICATIONS

This application claims priority to U.S. Ser. No. 60/792,245, filed Apr. 14, 2006. The contents of this application are incorporated herein by reference in their entirety.

STATEMENT AS TO FEDERALLY SPONSORED RESEARCH

This invention was made with government support under Grant Number DAMD17-02-1-045801 awarded by the Department of Defense Breast Cancer Research Program. The government has certain rights in the invention.

FIELD OF THE INVENTION

The invention relates generally to a method for assessing a response to anti-tumor treatment in a patient.

BACKGROUND OF THE INVENTION

Neoadjuvant (pre-operative) treatment is both a clinical trial model to compare the efficacy of first-line treatments and a translational research model to identify biomarkers and imaging methods that predict or monitor treatment response. A central tenet of neoadjuvant clinical trials is that tumor response should be strongly prognostic for patient survival. At present there are several different classifications of pathologic response being used in neoadjuvant trials. These variably account for tumor size, cellularity of the tumor bed, cytologic changes, in situ disease, and nodal burden; and they have varying degrees of patient survival data to suggest clinical validity.

Pathologic complete response (pCR) has been adopted as the primary endpoint for trials of neoadjuvant treatment for breast cancer because it is associated with long-term survival, and yet the definition of pCR is still not uniform. While it is generally held that a definition of pCR should include patients without residual invasive carcinoma in the breast (pT0), the presence of nodal metastasis, minimal residual cellularity, and residual in situ carcinoma are not consistently defined as pCR or residual disease (RD). When pCR is defined as no residual invasive cancer in the breast, the number of involved regional lymph nodes is inversely related to survival. Conversely, patients who convert to node-negative status after treatment have excellent survival, even if there is residual disease in the breast. Alternatively, the Miller and Payne classification ignores tumor size and nodal status altogether, and estimates only the decrease in cancer cellularity after treatment. This was also related to survival in a report including 176 patients. Two other classifications (Sataloff and Chevallier) also assess the post-treatment histologic and cytologic changes, although there is limited follow-up data to compare with survival. Reduction in cancer cellularity is generally greater when the residual tumor is small, suggesting that both size and cellularity provide response information. These different classifications suggest that reduction in the primary tumor size, regional nodal burden, and cellularity of the tumor bed all contribute meaningful pathologic response information.

It is imperative that pathologic response be defined with greatest prognostic relevance in order to optimize the clinical and scientific information that can be gained from neoadjuvant clinical trials. Dichotomization of response as pCR or residual disease (RD) is overly simplistic for these objectives, particularly because residual disease (RD) after neoadjuvant treatment includes a broad range of actual responses from near-pCR to frank resistance and disease progression.

SUMMARY OF THE INVENTION

The invention is based in part on the discovery of a quantitative histopathologic measure of residual cancer burden (RCB) post chemotherapy treatment that is strongly associated with survival and relapse risk in patients with breast cancer.

In one aspect, the invention features a method for predicting risk of relapse in a patient that had undergone therapy for a solid tumor by providing for a patient with a primary and metastatic tumor measurements $d_1$, $d_2$, $f_{cell}$, LN, and $d_{met}$, wherein $d_1$ and $d_2$ are bidimensional diameters of a primary tumor bed of the tumor in a resection specimen; $f_{cell}$, is the proportion of the primary tumor bed area that contains invasive carcinoma; LN is the number of regional lymph nodes containing metastatic carcinoma; and $d_{met}$ is the diameter of the largest metastasis in a regional lymph node. A residual cancer burden (RCB) index is calculated using the values for d1, $d_2$, $f_{cell}$, LN and $d_{met}$, and a prediction is made regarding the relapse risk of the patient based on the calculated RCB index where $d_{prim} = \sqrt{d_1 d_2}$.

In some embodiments, the RCB index is determined using $$RCB = 1.4(f_{inv}d_{prim})^{0.17} + [4(1-0.75^{LN})d_{met}]^{0.17}$$

In some embodiments, the solid tumor is a breast tumor.

In some embodiments, the RCB index is used to determine the extent of disease in a breast.

In some embodiments, the RCB index is used to determine the extent of disease in the regional lymph nodes (e.g. axillary, internal mammary, or infraclavicular sites in the case of breast cancer).

In some embodiments, the patient has multi-centric disease.

In some embodiments, the RCB index is calculated using largest primary tumor bed in the patient.

In some embodiments, the method further comprises classifying the subject for risk for residual disease based on the RCB index.

In some embodiments, the method further comprises determining the estrogen receptor (ER) status of the tumor.

In some embodiments, the RCB index is calculated using a computer.

Also provided by the invention is a method for predicting relapse risk in a patient undergoing therapy for a solid tumor. The invention includes providing from a patient with a primary and metastatic tumor $d_1$, $d_2$, $f_{cell}$; LN, $d_{met}$, and $\alpha$, wherein $d_1$ and $d_2$ are bidimensional diameters of a primary tumor bed of the tumor in a resection specimen; $f_{cell}$ is the proportion of the primary tumor bed area that contains invasive carcinoma; LN is the number of regional lymph nodes containing metastatic carcinoma; and $d_{met}$ is the diameter of the largest metastasis in an regional lymph node. A residual cancer burden (RCB) index is calculated using the values for d1, $d_2$, $f_{cell}$, LN and $d_{met}$, and a prediction is made regarding the survival of the patient based on the calculated RCB index, where $d_{prim} = \sqrt{d_1 d_2}$. The tumor can be, e.g., a breast tumor.

In some embodiments, the RCB index is determined using $$RCB = 1.4(f_{inv}d_{prim})^{0.17} + [4(1-0.75^{LN})d_{met}]^{0.17}$$

In some embodiments, the RCB index is used to determine the extent of disease in a breast.

In some embodiments, the RCB index is used to determine the extent of disease in the regional lymph nodes (e.g. axillary, internal mammary, or infraclavicular sites in the case of breast cancer).

In some embodiments, the patient has multi-centric disease.

In some embodiments, the RCB index is calculated using largest primary tumor bed in the patient.

In some embodiments, the method further comprises classifying the subject for risk for residual disease based on the RCB index.

In some embodiments, the method further comprises determining the estrogen receptor (ER) status of the tumor.

In some embodiments, the RCB index is calculated using a computer.

Also provided by the invention is software stored in a computer storage medium for predicting survival of a patient undergoing therapy for a solid tumor. The software is operable to receive for a patient with a primary and metastatic tumor data $d_1$, $d_2$, fcell; LN, $d_{met}$, as defined above, calculate a residual cancer burden (RCB) index using the $d_1$, $d_2$, $f_{cell}$, LN and $d_{met}$; and predict survival of the patient based on the RCB index. The tumor can be, e.g., a breast tumor.

In a further aspect the invention provides a system for predicting survival of a patient undergoing therapy for a solid tumor. The system includes at least one memory operable to store data for $d_1$, $d_2$, $f_{cell}$; LN, $d_{met}$, for a patient with a primary and metastatic tumor; and one or more processors, collectively operable to calculate a residual cancer burden (RCB) index using the $d_1$, $d_2$, $f_{cell}$, LN and $d_{met}$, as defined above. The tumor can be, e.g., a breast tumor.

Among the advantages of the invention is that it is performed using routine pathologic materials and methods of interpretation that are easily implemented in routine diagnostic practice.

The RCB index can be used to identify the most suitable treatment regimen for a tumor patient. For example, the RCB index can be monitored in a patient undergoing treatment for a tumor to determine if the treatment is effective.

The methods, software, and systems provided herein can be used to more accurately predict a response to a cancer treatment, quantify a response to a cancer treatment or treatments, and/or select the most appropriate cancer treatment or treatments for a subject. Thus, the methods, software, and systems can be used to more accurately can be used with any cancer treatment, e.g., surgical, radiation, chemotherapy (including hormonal or biologic therapy), and can be used in association with single modality or multiple modality treatments. RCB indices can be assessed before, during, or after completion of therapy. The methods, software, and systems provided herein can additionally be used to measure the effectiveness of a treatment, to identify biomarker(s) to test or predict effectiveness of the specific treatment, or to justify or otherwise verify the use of a predictive test that measures such effectiveness.

When measuring the effectiveness of treatment, the methods, software, and systems provided by the invention can additionally be used as a measure of the effectiveness of a new treatment or new combination of treatments, or to demonstrate improved patient outcome from the new treatment or combination of treatments.

The methods, software, and systems described herein can additionally be used with other methods or markers to assess the presence and/or progression of tumor. For example, an RCB index can be used in combination with other markers such as genomic or standard protein assays to predict survival, response or relapse in cancer.

A further use of the methods, software, and systems described herein is in drug development clinical trials to set more accurate benchmarks of pharmacogenomic responses in evaluations of anti-tumor treatments, including new anti-tumor drug treatments.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1. Pathological assessment of residual cancer in surgical resection specimens. Measurements include the bidimensional diameters of the primary tumor bed (d1, d2), the proportion of the primary tumor area that contains invasive carcinoma, the number of regional lymph nodes containing metastatic carcinoma, and the diameter of the largest metastasis in a lymph node (dmet). Table: coefficients of multivariate Cox regression model for predicting the risk distant relapse in the T/FAC treated cohort.

(FIG. 2A) Risk curve for entire cohort; (FIG. 2B) Risk curves by adjuvant hormonal treatment status (thicker lines represent group who received hormonal treatment). All hormone receptor (HR) positive patients were eligible for the treatment and 91% of them underwent adjuvant hormonal therapy.

(FIG. 4A) Percent of invasive cancer; (FIG. 4B) Mean diameter of primary tumor bed in cm; (FIG. 4C) Number of positive lymph nodes; (FIG. 4D) Diameter of largest metastasis in cm.

(FIG. 5A) Entire development cohort of 241 T/FAC-treated patients; (FIG. 5B) Patients who did not receive adjuvant hormonal treatment (100% of hormone receptor (HR) negative and 9.1% of HR positive patients were in this group); (FIG. 5C) Patients who received adjuvant hormonal treatment (90.9% of HR positive patients and no HR negative patients were in this group). P values are from a log-rank test for difference between all survival curves.

(FIG. 6A) AJCC Stage-I; (FIG. 6B) AJCC Stage-II; (FIG. 6C) AJCC Stage-III. AJCC Stage-0 is equivalent as RCB-0 and complete pathologic response (pCR). The P values are from a log-rank test for difference between survival curves.

(FIG. 7A) development cohort of T/FAC treated patients; (FIG. 7B) validation cohort of FAC treated patients. Symbols: crosses represent unadjusted model; filled circles represent optimism-adjusted model through global shrinkage factor.

(FIG. 8A) Risk curve for entire FAC-treated cohort; (FIG. 8B) Risk curves by adjuvant hormonal treatment status (thicker lines represent group that received hormonal treatment). See FIG. 2 for further details.

(FIG. 9A) Entire development cohort of 141 FAC-treated patients; (FIG. 9B) Patients who did not receive adjuvant hormonal treatment (94.3% of hormone receptor (HR) negative and 33.7% of HR positive patients were in this group); (FIG. 9C) Patients who received adjuvant hormonal treatment (66.3% of HR positive patients and 5.7% of HR negative patients were in this group). P values are from a log-rank test for difference between all survival curves.

(FIG. 10A) AJCC Stage-I; (FIG. 10B) AJCC Stage-II; (FIG. 10C) AJCC Stage-III. AJCC Stage-0 is equivalent as RCB-0 and complete pathologic response (pCR). The P values are from a log-rank test for difference between survival curves.

DETAILED DESCRIPTION OF THE INVENTION

Figure 2A:
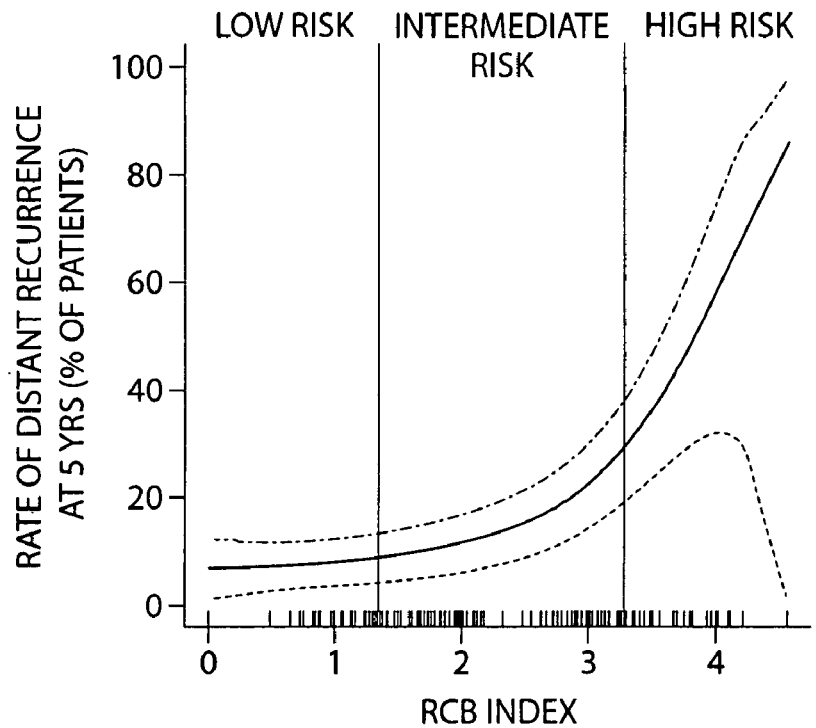
FIGS. 2A-B. Likelihood of 5-year distant recurrence as a continuous function of RCB estimated from the patient cohort that received neoadjuvant T/FAC treatment. The continuous function was generated using a smoothing spline approximation of RCB. The plots show the estimated 5-year relapse rate (solid curves) and the corresponding point-wise 95% confidence interval (dashed lines)

The invention provides a metric based on routine pathologic materials for quantifying and classifying response to treatment in order to help design targeted diagnostic tools for treatment selection and to evaluate outcome of chemotherapy trials.

In general, the metric can be applied to a subject diagnosed with, or at risk for, any tumor that is amenable to measurement with the parameters described below. Thus, the tumor can be, e.g., a solid tumor, including a metastatic tumor. The solid tumor can be, e.g., a carcinoma (including adenocarcinoma and squamous cell carcinoma), a sarcoma, or a lymphoma. Examples of suitable solid tumors include cervical cancer, breast cancer, lung cancer (including small cell and large cell lung carcinoma), liver cancer, prostate cancer, colon cancer, renal cancer, pancreatic cancer, cervical cancer, ovarian cancer, cancer of the central nervous system and melanoma.

The strength of association between tumor response and survival is critical for evaluation of chemotherapy trials and for selection of appropriate treatment for an individual diagnosed with a tumor. Pathologic complete response (pCR), an endpoint used as a surrogate for survival in pre-operative chemotherapy, reliably predicts survival benefit, but residual disease (RD) or non-pCR, contains a range of pathologic responses that likely contain different prognostic groups, including near complete response and resistance. By using these endpoints for evaluation of trials or for design of treatment-directed diagnostics, patients potentially in high-response sections of residual disease will be treated as similar to those with no tumor shrinkage. Residual cancer burden (RCB) combines information obtained from routine pathologic study of the post-treatment surgical resection specimen and calculates an index of the extent of residual disease in the breast and regional lymph nodes.

An RCB index is calculated by measuring certain properties of primary and metastatic tumors in a patient. The parameters include bidimensional diameters of the primary tumor bed in the resection specimen ($d_1$ and $d_2$) measured in millimeters, the proportion of the primary tumor bed area that contains invasive carcinoma ($f_{cell}$) as estimated from microscopic review of the tumor bed slides, the number of regional lymph lymph nodes containing metastatic carcinoma (LN), and the diameter of the largest metastasis in an regional lymph node ($d_{met}$) measured in millimeters.

Histopathologic parameters can be determined using methods known in the art and can be obtained from either fresh or preserved specimens. For example, histopathologic parameters can be determined from reviews of pathology reports, including routine hematoxylin and eosin (H&E) stained slides of the post-treatment surgical resection specimen.

If patients have multi-centric disease, then the largest primary tumor bed is preferably evaluated.

The parameters are then combined to estimate the residual cancer burden (RCB). Preferably the RCB is calculated after neoadjuvant treatment as the sum of residual cancer in the primary tumor bed and regional lymph nodes.

The primary and metastatic terms can be exponentially transformed to approximate normality and then scaled, e.g., to match the 95$^{th}$ percentiles of transformed primary and metastatic distributions.

In one embodiment, the residual cancer burden index is defined in terms of contributions from the primary tumor bed and metastases to lymph nodes as follows:

$$RCB=1.4(f_{inv}d_{prim})^{0.17}+[4(1-0.75^{LN})d_{met}]^{0.17}, \quad (1)$$

where $f_{cell}$ is the cellularity fraction of the primary tumor bed (with values between 0 and 1), $d_1$, $d_2$ are the primary and secondary tumor bed dimensions (in mm), the bidimensional measurements of the primary tumor bed were combined as follows: $d_{prim}=\sqrt{d_1 d_2}$, $d_{met}$ is the diameter of the largest positive lymph node (in mm), and LN is the number of positive lymph nodes. In (1) above, the exponent of 0.17 is the optimal exponent of the Box-Cox power transformation to transform the primary and metastatic terms to approximate normality. A factor (1.4) is introduced to adjust the scale the two terms by matching the 95-th percentiles of the transformed distributions.

Additional methods for determining an RCB index are shown in Example 8.

If desired, the RCB index is calculated using a computer.

Calculation of residual cancer burden (RCB) as a continuous measure of response is strongly prognostic, and can be a useful parameter of response. As is discussed in the Examples, below, of the three classes of RCB that describe minimal residual disease, RCB-I identifies about 17% of patients with prognosis at 5 years that is similar to pCR. RCB has more prognostic power than Stage and better defines the near-pCR and resistant groups. The prognostic power of RCB was maintained in two studies involving different chemotherapy regimens, and in ER-positive and ER-negative disease.

Residual cancer burden (RCB) combines information obtained from routine pathologic evaluation of the post-treatment surgical resection specimen and calculates an index of the extent of residual disease in the breast and regional lymph nodes. The variables used to calculate RCB can be simply obtained from pathologic review and are entered into a calculation script that is freely available. Quantification of residual disease implies that the responses from different arms of a neoadjuvant study can be directly compared on a continuous scale. This offers potential advantages in that all subject responses contribute to the analysis, so treatment regimens with low pCR rates (such as hormonal therapy) or smaller phase II studies could be compared to identify differences in the extent of RD.

The calculation of residual cancer burden (RCB) from routine pathologic resection materials is a practical method to quantify residual disease. RCB as a continuous measure of response is strongly prognostic, and this could become a useful parameter of response. The four classes of RCB that we have defined are useful to identify pCR (RCB-0), minimal residual disease (RCB-I) in about 17% of patients with prognosis at 5 years that is similar to pCR, and chemoresistance (RCB-III) in 13% of patients with associated poor prognosis. Although the information used to calculate RCB and AJCC Stage is quite similar, RCB has more prognostic power than Stage and better defines the near-pCR and resistant groups.

The prognostic power of RCB was maintained in two neoadjuvant chemotherapy studies, and in ER-positive and ER-negative disease. Therefore, RCB is a robust measure of response.

If desired, a patient's residual cancer burden prior to treatment with the RCB index can include dimensions of the primary tumor from imaging or other clinical examinations. Additional parameters that can be combined in the RCB index include, e.g., tumoral involvement of the lymph nodes available from imaging, clinical exam, or biopsy and histopathologic parameters from a biopsy such as cellularity, grade, estrogen receptor status, progesterone receptor status, oncogene status or diagnostic class.

The invention will be further illustrated in the following non-limiting examples. In this work pathologic slides and reports were reviewed from 382 patients in two completed pre-operative (neoadjuvant) trials: 1) fluorouracil, doxorubicin and cyclophosphamide (FAC) in 141 patients, and 2) paclitaxel followed by FAC (T/FAC) in 241 patients. Paclitaxel was administered as twelve weekly or four 3-weekly cycles. Residual cancer burden (RCB) was calculated as an index that combines pathologic measurements of primary tumor (size and cellularity) and nodal metastases (number and size). We compared four RCB categories, from RCB-0 (pCR) to RCB-3 (chemoresistant), versus post-treatment revised AJCC Stage (0-III) for prediction of distant relapse-free survival (DRFS) in multivariate Cox regression analyses.

RCB was independently prognostic in a multivariate model that included age, pre-treatment clinical Stage, hormone receptor status and hormonal therapy, and pathologic response (pCR versus RD) (HR=2.50, CI 1.70-3.69, P<0.001). Minimal RD (RCB-I) in 17% of patients carried the same prognosis as pCR (RCB-0). Extensive RD (RCB-III) in 13% of patients was associated with poor prognosis, regardless of hormone receptor status, adjuvant hormonal therapy, or pathologic AJCC Stage of residual disease. The generalizability of RCB for prognosis of distant relapse was confirmed in the FAC-treated validation cohort. The resistant category RCB-3 was a stronger predictor of relapse than AJCC Stage III and identified a larger group of high-risk patients (see Examples).

Example 1

General Methods

Patients and Materials

Pathology reports and hematoxylin and eosin (H&E) stained slides were reviewed from the surgical resection specimens of 382 patients who completed neoadjuvant chemotherapy for noninflammatory, invasive breast carcinoma (T1-3, N0-1, M0). One cohort included 241 patients who received six months of neoadjuvant chemotherapy with a regimen including paclitaxel, 5-fluorouracil, doxorubicin, and cyclophosphamide (T/FAC) followed by surgical resection of the residual tumor with negative margins and either sentinel lymph node biopsy procedure or axillary dissection (protocol MDACC DM 98-240) (Green et al., 2005). Patients in this trial were randomized to receive preoperative chemotherapy consisting of paclitaxel (T) given at 3-weekly intervals (225 mg/m2) or weekly for 12 cycles (150 mg/m2 for node positive patients or 80 mg/m2 for node negative patients) (Green et al., 2005). The paclitaxel courses were followed by four cycles of FAC (5-fluorouracil 500 mg/m2, doxorubicin 50 mg/m2 and cyclophosphamide 500 mg/m2) given at 3-weekly intervals. Their baseline and post-treatment characteristics are shown in Table 1. The median age of the cohort was 51 years and consisted predominantly of patients with large (mean size 2.5 cm) Stage II/III tumors (90%). The pathologic complete response (pCR) rate in this group after 6 months of T/FAC chemotherapy was 23% and there was almost a 50% reduction in the fraction of invasive cancer and in the size of the primary tumor. The median follow-up was 67.3 months and 16% of the patients developed distant metastasis within 5 years from initial diagnosis. Data from patients in this cohort were used to develop the formula for residual cancer burden index and to identify thresholds of RCB that identify corresponding risk groups.

The other cohort had longer follow-up and included 141 patients who received three months of neoadjuvant chemotherapy with four cycles of FAC given at 3-weekly intervals (225 mg/m2), followed by surgical resection of the residual tumor with negative margins and axillary dissection, and then three additional months of adjuvant chemotherapy that was FAC in 129, and other non-cross-resistant chemotherapy in 12 who had clinically stable or progressive disease (see Table 1). Data from patients in this cohort were used for validation of the residual cancer burden index. This cohort included patients with more advanced disease (63% node-positive, versus 47%; 100% Stage II/III, versus 90%) and larger size tumors (3.9 cm, versus 2.5 cm). The pCR rate was lower in the validation cohort (16%), consistent with the shorter duration of pre-operative chemotherapy. The median follow-up in this cohort was 104.7 months and 20% of the patients developed distant metastases within 5 years. There were fewer censored observations in this cohort at 5 years due to the longer follow-up.

Patients with hormone receptor-positive breast cancer were offered 5 years of adjuvant (postoperative) tamoxifen according to treatment guidelines at the time. The Institutional Review Board of MDACC approved these protocols and all patients signed an informed consent prior to initiation of therapy.

TABLE 1

Population Characteristics of the Cohorts used for Development and Validation of the Residual Cancer Burden Index.

| Characteristic | T/FAC Cohort (n = 241) | FAC Cohort (n = 141) |
|---|---|---|
| Treatment | | |
| Neoadjuvant treatment | | |
| T/FAC† | 241 (100%) | 0 (0%) |
| FAC‡ | 0 (0%) | 141 (100%) |
| Adjuvant hormonal treatment§ | | |
| Yes | 160 (66%) | 57 (40%) |
| No | 81 (34%) | 80 (57%) |
| Unknown | 0 (0%) | 4 (3%) |
| Demographic and Clinical | | |
| Age (years) | | |
| Mean (SD) | 50.8 (10.6) | 48.8 (10.4) |
| ≦50 | 119 (49%) | 79 (56%) |
| >50 | 122 (51%) | 62 (44%) |
| ER status | | |
| Positive | 151 (63%) | 79 (56%) |
| Negative | 90 (37%) | 55 (39%) |
| Unknown | 0 (0%) | 7 (5%) |
| PR status | | |
| Positive | 112 (47%) | 57 (40%) |
| Negative | 126 (52%) | 51 (36%) |
| Unknown | 3 (1%) | 33 (23%) |
| HER2 status | | |
| Positive | 49 (20%) | 0 (0%) |
| Negative | 181 (75%) | 3 (2%) |
| Unknown | 11 (5%) | 138 (98%) |
| Tumor Pathology Before Neoadjuvant Rx | | |

TABLE 1-continued

Population Characteristics of the Cohorts used for Development and Validation of the Residual Cancer Burden Index.

| Characteristic | T/FAC Cohort (n = 241) | FAC Cohort (n = 141) |
|---|---|---|
| Lymph node status | | |
| Positive | 114 (47%) | 89 (63%) |
| Negative | 127 (53%) | 52 (37%) |
| AJCC stage | | |
| 0 | 0 (0%) | 0 (0%) |
| I | 23 (10%) | 0 (0%) |
| II | 196 (81%) | 76 (54%) |
| III | 22 (9%) | 65 (46%) |
| Invasive cancer in primary tumor bed (%) | | |
| Mean (SD) | 36.8 (19.7) | 47.6 (25.1) |
| Unknown | 67 (28%) | 48 (20%) |
| Primary tumor bed size¶ (mm) | | |
| Mean (SD) | 24.9 (13.5) | 39.2 (17.1) |
| Unknown | 39 (16%) | 12 (5%) |

Pathological Assessment

The following variables were assessed from our review of pathology reports and routine hematoxylin and eosin (H&E) stained slides of the post-treatment surgical resection specimen: bidimensional diameters of the primary tumor bed in the resection specimen ($d_1$ and $d_2$) measured in millimeters, the proportion of the primary tumor bed area that contains invasive carcinoma ($f_{cell}$) as estimated from microscopic review of the tumor bed slides, the number of regional lymph nodes containing metastatic carcinoma (LN), and the diameter of the largest metastasis in an regional lymph node ($d_{met}$) measured in millimeters. The bidimensional measurements of the primary tumor bed were combined as follows: $d_{prim} = \sqrt{d_1 d_2}$. If patients were reported to have multi-centric disease, then the largest primary tumor bed was evaluated.

To estimate the proportion of invasive carcinoma ($f_{inv}$) within the cross sectional area of the primary tumor bed, we first estimated the overall percent area of carcinoma (% CA) from microscopic review of the corresponding slides and then corrected for the component of in situ carcinoma (% CIS): $f_{inv} = (1-(\% CIS)/100) \times (\% CA)/100$. To estimate the extent of residual cancer in the regional lymph nodes, we reviewed the slides from resected axillary lymph nodes and recorded the number of lymph nodes that contained a metastasis (LN), and the greatest diameter of the largest metastasis ($d_{met}$). The variables were then combined to estimate the residual cancer burden (RCB) after neoadjuvant treatment as the sum of residual cancer in the primary tumor bed and axillary lymph nodes. We exponentially transformed the primary and metastatic terms to approximate normality and then scaled these two terms to match the $95^{th}$ percentiles of transformed primary and metastatic distributions from the T/FAC dataset.

Statistical Methods

Distant relapse-free survival (DRFS) was recorded as the interval from initial diagnostic biopsy until distant metastasis. If there was no relapse event, then the patient was censored at the time of last follow-up. Death before distant relapse was considered as a censoring event. Only data from the T/FAC treated cohort were used in the described analyses to characterize the RCB index and to determine the cut points for the different RCB groups. Covariate effects on distant relapse risk were evaluated in multivariate Cox proportional hazards analyses. None of the covariates exhibited significant deviations from the proportionality assumption or had time-dependent effects (Feldman et al, 1986). The incremental contribution of the continuous RCB index was evaluated by comparing multivariate Cox models without or with a linear RCB term and its statistical significance was assessed based on the likelihood ratio test. The functional form of the dependence of the 5-year distant relapse risk on the RCB index was determined through a univariate Cox proportional hazards model of DRFS having as the only covariate a smoothing spline approximation of the RCB index with 2 degrees of freedom. (1) The baseline cumulative hazard rate was estimated from the Cox model based on the Nelson-Aalen estimator and the predicted rate of distant relapse at 5 years was then obtained from the Breslow-type estimator of the survival function. Point-wise confidence intervals of the survival estimate were calculated based on the Tsiatis variance estimates of the cumulative log-hazards (Feldman et al., 1986).

Definition of Residual Cancer Burden Index

An exemplary residual cancer index is defined in terms of contributions from the primary tumor bed and metastases to lymph nodes as follows:

$$RCB=1.4(f_{inv}d_{prim})^{0.17}+[4(1-0.75^{LN})d_{met}]^{0.17}, \quad (1)$$

where $f_{cell}$ is the cellularity fraction of the primary tumor bed (with values between 0 and 1), $d_1$, $d_2$ are the primary and secondary tumor bed dimensions (in mm), $d_{prim}=\sqrt{d_1d_2}$, $d_{met}$ is the diameter of the largest positive lymph node (in mm), and LN is the number of positive lymph nodes. The exponent of 0.17 is the optimal exponent of the Box-Cox power transformation to transform the primary and metastatic terms to approximate normality (data not shown). A factor (1.4) was introduced to adjust the scale the two terms by matching the 95-th percentiles of the transformed distributions.

The four parameters of residual tumor ($d_{prim}$, $f_{inv}$, LN, and $d_{met}$) were individually associated with significantly higher risk of distant relapse (p<0.001) after T/FAC chemotherapy. These covariates maintained significance as independent predictors of relapse risk in a multivariate Cox regression model (FIG. 1). To calculate a single index of residual cancer burden, we first combined the covariates to terms that measure residual cancer burden in the primary tumor bed ($RCB_{prim}=f_{inv}d_{prim}$) and in regional metastases ($RCB_{met}=4(1-0.75^{LN})d_{met}$). The metastatic term is intended to be proportional to the sum of diameters of the affected lymph nodes, but since only the size of the largest metastasis is routinely measured we modeled the size distribution of lymph node metastases. The specific term used above is based on a subjective but empirically reasonable assumption that additional nodal metastases each have 75% of the diameter of the next-largest metastasis.

Assessment of RCB Index as a Predictor of Relapse Risk

We confirmed that the primary and metastatic contributions to the RCB index were independently and significantly associated with relapse risk after adjusting for other risk factors in multivariate Cox regression analysis (primary term HR: 2.84, 95% CI: 1.47-5.48, P=0.002; metastatic term HR: 2.57, 95% CI: 1.58-4.17, P<0.001). The magnitude of the hazard ratios suggests that both terms contribute similarly to the predictive power of the RCB index.

Figure 2B:
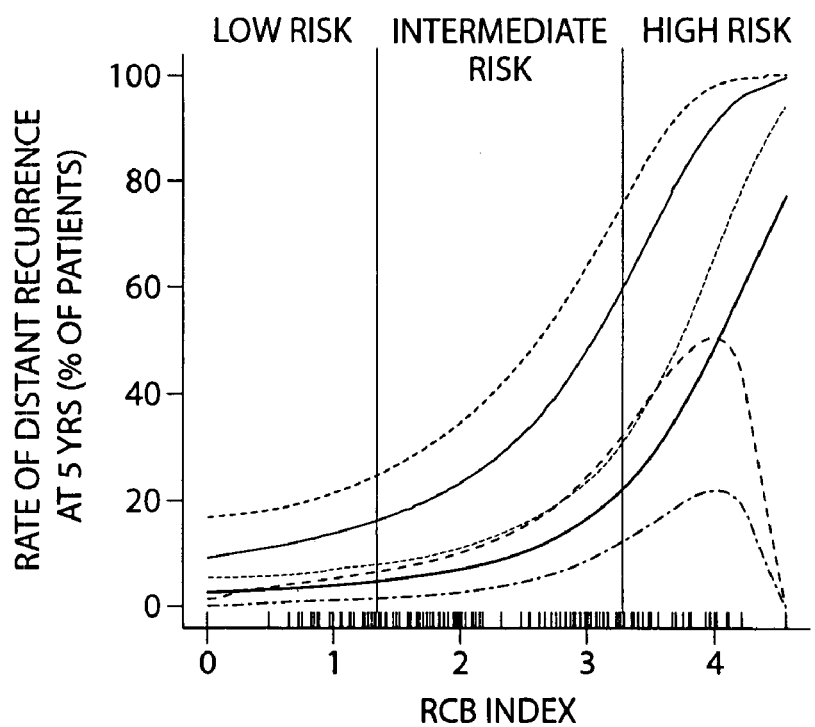
Figure 3:
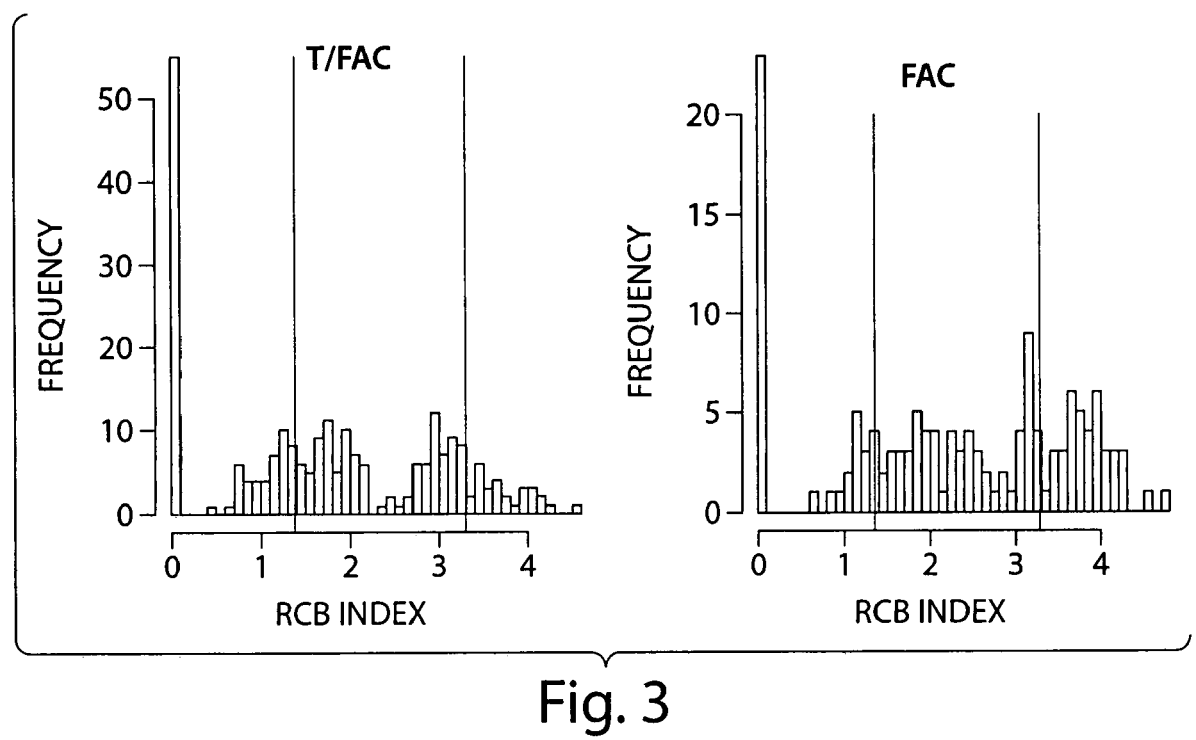
FIG. 3. Distribution of RCB index among the patients treated with neoadjuvant T/FAC (left) or FAC (right). The bar at RCB=0 represents individuals who achieved complete pathologic response (pCR). The vertical lines show the optimal cut points determined from the T/FAC data.

We modeled the functional dependence of the relapse risk on the values of the RCB index using smoothing splines that were estimated in a Cox regression model. There appeared to be an exponential-like increase in the likelihood of 5-year distant relapse with increasing RCB values when T/FAC chemotherapy was administered pre-operatively (FIG. 2A). A similar analysis stratified by hormonal-treatment status demonstrated an overall increased risk of relapse with increasing RCB levels for hormone receptor negative breast cancer patients who did not receive adjuvant hormonal therapy (FIG. 2B). The likelihood of 5-year relapse in patients who received hormonal treatment was lower for the entire range of RCB values, and it increased more gradually through the lower spectrum of RCB values (FIGS. 2A, 2B). However, both groups had similar gradients of increasing risk through the higher spectrum of RCB values, indicating comparatively greater risk of relapse with more extensive residual disease.

The RCB index and clinical covariates were individually evaluated as risk factors for disease relapse in univariate Cox regression analyses of the 241 patients who received six months of pre-operative T/FAC chemotherapy. All covariates were significantly associated with distant relapse (Table 3). Specifically, women aged 50 or less, with clinical Stage III or hormone receptor-negative cancer, who did not receive adjuvant hormonal treatment, or had residual disease (RD) after neoadjuvant T/FAC treatment had a significantly higher risk of distant relapse. In addition, the continuous RCB index was strongly associated with distant relapse risk with patients having over a two-fold increase in relapse risk for each unit of increase in the RCB index (HR: 2.50, 95% CI: 1.70-3.69, P<0.001).

Example 2

Definition of Risk Groups Based on Cut-Point Analysis

Response to neoadjuvant chemotherapy is an intermediate endpoint for breast cancer relapse and survival. The most commonly used systems for breast cancer response classify response as complete pathologic response (pCR) and residual disease. The RCB index, which includes pathologic assessment of both the primary breast tumor and of the regional lymph nodes, can provide a basis for further classification of residual disease in prognostic categories.

By design of the RCB index, RCB=0 scores correspond to complete pathologic response. It is clear from FIG. 2B that subjects with high levels of residual disease (e.g. RCB score>~3) after neoadjuvant T/FAC chemotherapy have a considerably higher risk of disease relapse and therefore poor long-term prognosis. Furthermore, another subgroup of patients with low levels of residual disease (e.g. 0<RCB<~2) are associated with very low risk of disease relapse, with similar prognosis as the pCR subgroup.

Figure 4A:
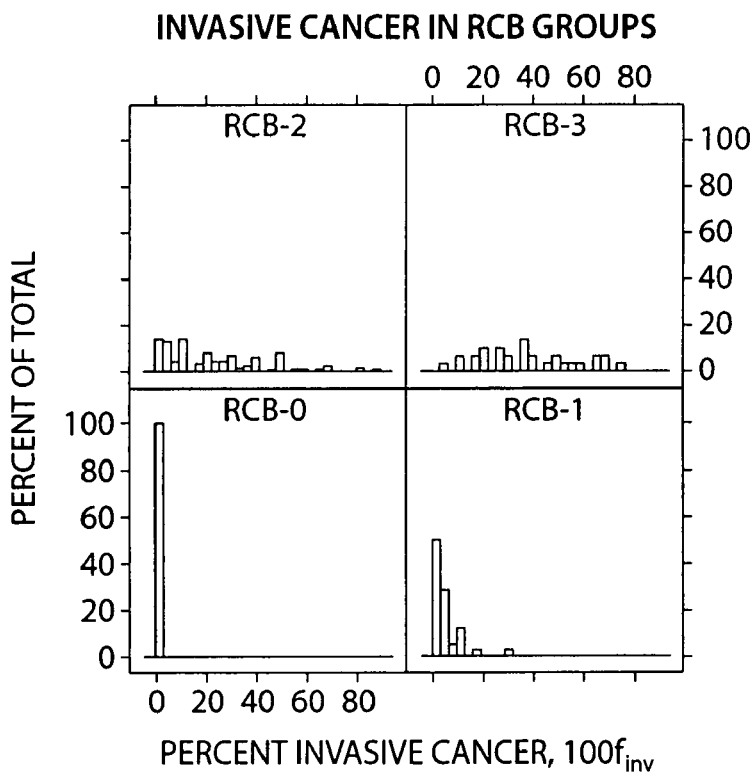
FIGS. 4A-D. Distributions of pathological characteristics of residual disease within the four RCB groups.
Figure 4B:
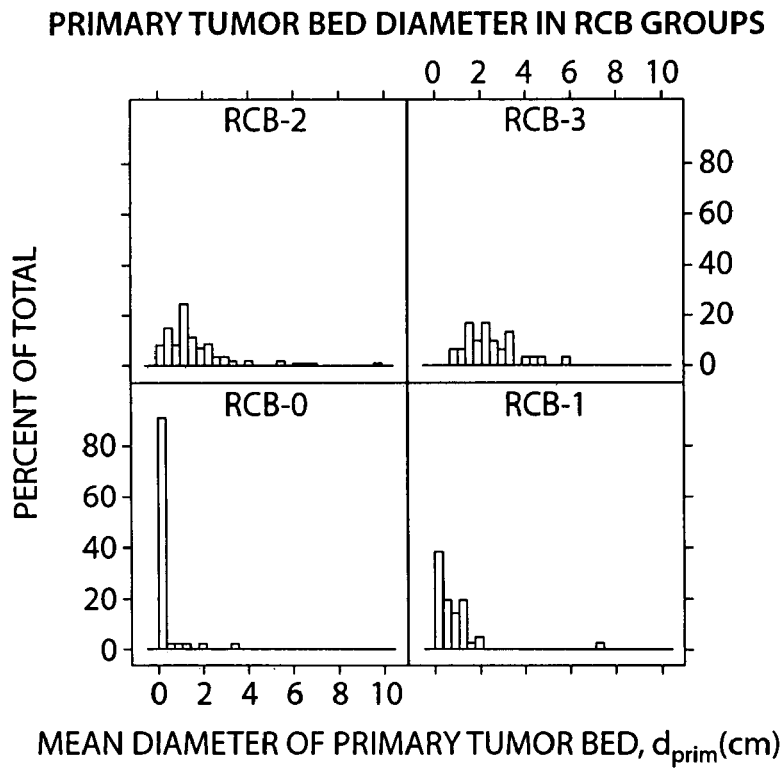
Figure 4C:
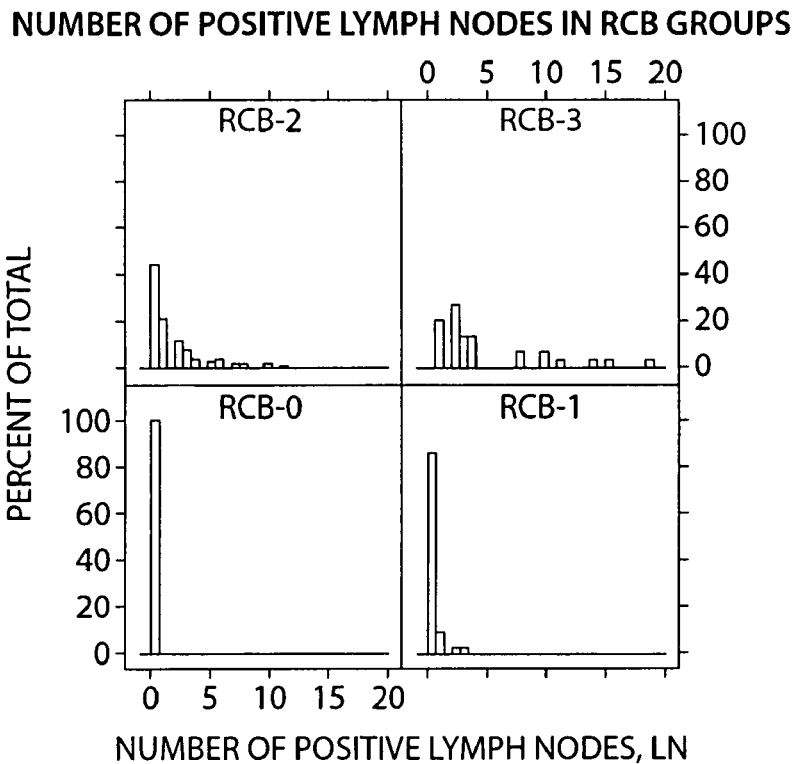
Figure 4D:
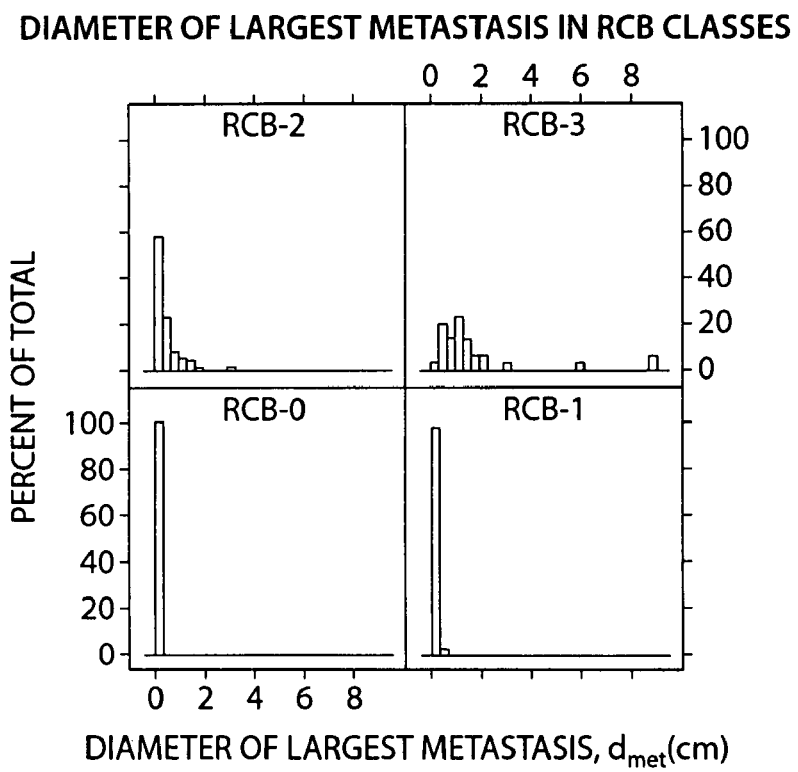

Two cut points were selected to categorize patients with residual disease (RCB>0) among the 241 T/FAC patients into three subgroups with increasingly poor prognosis, thus defining four subgroups: RCB-0 (pCR), RCB-I (minimal residual disease), RCB-II (moderate residual disease), and RCB-III (extensive residual disease). To determine the first cut point, we fit a multivariate Cox regression model that included all the clinical covariates and a dichotomized RCB factor. The optimal cut point was selected from the range between the 5 percent to the 95 percent quantile of the distribution of RCB as the quantile that maximized the profile log-likelihood of this model. This occurred at the value of 3.28 that corresponds to the $87.5^{th}$ quantile of the RCB distribution in this cohort. A second cut point was determined similarly by maximizing the profile log-likelihood of a Cox model that included all clinical covariates and the dichotomized RCB factor. This cut point occurred at the value of 1.36 or the $40^{th}$ quantile of the RCB distribution. The cut points defined subgroups of RCB-0 to RCB-III with increasingly poor prognosis (Table 2, FIG. 4A). The Kaplan-Meier estimate of the fraction of patients who did not relapse within 5 years was 94.6% for the pCR group and 97.6% for the group with minimal residual disease (RCB-I), whereas it was only 46.4% for the group with extensive residual disease (RCB-III). The difference in the rates of distant relapse between these groups was significant (P<0.001 by the log-rank test).

TABLE 2

Kaplan-Meier Estimates of the Rate of Distant Relapse at 5 Years According to Residual Disease Categories Defined Based On the Residual Cancer Burden Index.

| Categories of Residual Cancer Burden | Development Cohort (T/FAC) (n = 241) | | Validation Cohort (FAC) (n = 141) | | |
|---|---|---|---|---|---|
| | Percentage of Population | Rate of Distant Relapse at 5 Years (95% CI)‡ | Percentage of Population | Rate of Distant Relapse at 5 Years (95% CI) | Rate of Distant Relapse at 10 Years (95% CI) |
| Pathologic Complete Response (RCB-0) | 22.8 | 5.4 (1.8-16.0) | 16.3 | 0.0† | 0.0† |
| Minimal Residual Disease (RCB-I) | 17.4 | 2.4 (0.0-16.1) | 11.3 | 0.0† | 23.1 (5.7-68.8) |
| Moderate Residual Disease (RCB-II) | 47.3 | 16.2 (10.5-24.5) | 44.7 | 22.9 (14.3-35.6) | 37.6 (26.5-51.5) |
| Extensive Residual Disease (RCB-III) | 12.5 | 53.6 (37.1-71.9) | 27.7 | 36.8 (23.6-54.2) | 54.5 (39.3-71.2) |

‡Confidence intervals are based on Greenwood variance estimate on the log-log scale
†No relapse events in this group within 5 years The intrinsic prognostic potential of the RCB system was quantified by the difference in the rates of distant relapse at 5 years between the groups with the worst (RCB-III) and best (RCB-0) prognosis. This difference, which is closely related to the positive and negative predictive values of a diagnostic test (Altman and Royston, 2000), was 48.2% (95% CI 8.0-80.1) indicating a sufficiently reliable performance for classification of patients in different prognostic groups.

FIG. 4 indicates that the minimal residual disease groups RCB-0 and RCB-I are very homogeneous, with the RCB-I group consisting primarily of node-negative tumors or node positive tumors with small size of metastasis. On the other end, the moderate and extensive residual disease groups, RCB-II and RCB-III are considerably more heterogeneous and include tumors with a broad range of pathological characteristics, which however occur in combinations that result in similar prognosis. As expected, the RCB-III group consists of individuals with the largest and most invasive tumors or those with a large number of positive lymph nodes or large metastases. Data in FIG. 4 are from the T/FAC treated cohort.

The significance of RCB index as an independent predictor of disease relapse was also assessed based on the separation probability, defined as the difference between the relapse probabilities for a patient in the group with the worst prognosis (RCB-III) and a patient in the group with the best prognosis (RCB-0) (Altman and Royston, 2000). The relapse probabilities were obtained from the Kaplan-Meier survival estimates and the confidence intervals were based on the cumulative log-hazard estimate of the variance. To evaluate whether knowledge of a tumor's RCB class after chemotherapy adds new independent prognostic information to the revised AJCC stage, we performed separate Kaplan-Meier analyses by RCB class within each AJCC stage stratum. The significance of the additional stratification provided by the RCB class was evaluated based on the log-rank test.

We evaluated the accuracy of RCB-based model for prognosis of disease relapse by assessing its calibration and discrimination (Altman and Royston, 2000). Calibration of the full multivariate Cox model was evaluated by comparing the predicted probabilities of distant relapse to the Kaplan-Meier survival estimates at 5 years in patient groups defined by the quintiles of predicted survival. Bias or overoptimism in the predicted probabilities introduced by selecting optimal RCB cut points from the same data was estimated using bootstrap resampling of the data with 300 replications (Harrell, 2001). The linear predictor of the Cox model was shrunk by the estimated shrinkage factor ($<1$) and the shrunken model was then used for obtaining unbiased estimates of relapse-free survival in the independent validation cohort. Model discrimination was evaluated based on Harrell's concordance index, or c index, which is a generalized area under the receiver operating curve (AUC) for censored observations and is equal to the probability of concordance between the predicted probability of relapse and the relapse outcome (Harrell, 2001). The concordance index was adjusted for bias using bootstrap resampling with 300 replications. The confidence interval for the c index was obtained based on approximate normality using the variance estimate of the unadjusted index.

Example 3

RCB Classification Versus Clinical Parameters for Predicting Distant Relapse Patient age, tumor stage, chemotherapy regimen, and pathologic response status were independent predictors of distant relapse in a multivariate Cox regression model that included clinical and treatment covariates but did not include RCB index as a predictor (Tables 3 and 4). When the RCB index was included, age (P=0.01) and chemotherapy regimen (P=0.03) were still significantly associated with relapse risk, but the clinical stage before treatment and the binary pathologic response (pCR vs. RD) were not. The RCB index was significantly associated with the risk of disease recurrence, even after adjusting for the additional covariates (HR: 2.50, 95% CI: 1.70-3.69, P<0.001 for TFAC cohort) (Table 3), and it improved significantly the overall predictive power of the multivariate Cox model (P<0.001). It has been recommended that the predictive ability of a new marker should be evaluated based on whether the marker improves an already optimized multivariate model of available risk factors (Kattan, 2003). On this basis the RCB index is an independent new risk factor that improves prediction of distant relapse in T/FAC treated patients compared to currently used risk factors.

TABLE 3

Multivariate Cox Proportional Hazards Analyses of Prognostic Factors
of Distant Relapse Free Survival in T/FAC Treated Cohort.

|  | Analysis without RCB Index | | Analysis with RCB Index‡ | |
|---|---|---|---|---|
| Variable | Hazard Ratio (95% CI) | P value | Hazard Ratio (95% CI) | P value |
| Age (>50 vs ≦50) | 0.32 (0.16-0.64) | 0.001 | 0.41 (0.20-0.83) | 0.01 |
| Stage Pre (III vs I or II) | 3.01 (1.33-6.84) | 0.008 | 2.27 (0.96-5.35) | 0.06 |
| Hormone Receptor Status† (P vs N) | 0.48 (0.14-1.67) | 0.25 | 0.54 (0.16-1.85) | 0.33 |
| Hormonal Rx (Y vs N) | 0.54 (0.16-1.85) | 0.33 | 0.33 (0.09-1.16) | 0.08 |
| Paclitaxel Schedule (3-weekly vs weekly) | 1.50 (1.08-2.08) | 0.02 | 1.48 (1.04-2.04) | 0.03 |
| Response (RD vs pCR) | 4.82 (1.77-13.1) | 0.002 | 0.54 (0.12-2.32) | 0.41 |
| RCB Index | — | — | 2.50 (1.70-3.69) | <0.001 |

†Defined as positive if ER-positive or PR-positive
‡P-value < 0.001 and chi-square = 24.8 (by the likelihood ratio test) for the comparison with the analysis without the RCB index

TABLE 4

Multivariate Cox Proportional Hazards Analyses of Prognostic
Factors of Distant Relapse Free Survival in FAC Treated Cohort (n = 118).

|  | Analysis without RCB Index | | Analysis with RCB Index‡ | |
|---|---|---|---|---|
| Variable | Hazard Ratio (95% CI) | P value | Hazard Ratio (95% CI) | P value |
| Age (>50 vs ≦50) | 1.31 (0.65-2.63) | 0.46 | 1.10 (0.53-2.34) | 0.78 |
| Stage Pre (III vs I or II) | 3.21 (1.64-6.29) | <0.001 | 2.78 (1.37-5.62) | 0.004 |
| Hormone Receptor Status† (P vs N) | 1.16 (0.45-2.99) | 0.77 | 0.54 (0.18-1.58) | 0.26 |
| Hormonal Rx (Y vs N) | 1.10 (0.47-2.57) | 0.82 | 0.96 (0.40-2.31) | 0.93 |
| RCB Index | — | — | 2.11 (1.46-3.05) | <0.001 |

†Defined as positive if ER-positive or PR-positive
‡P-value <0.001 and chi-square = 19.4 (by the likelihood ratio test) for the comparison with the analysis without the RCB index Example 4

Figure 5A:
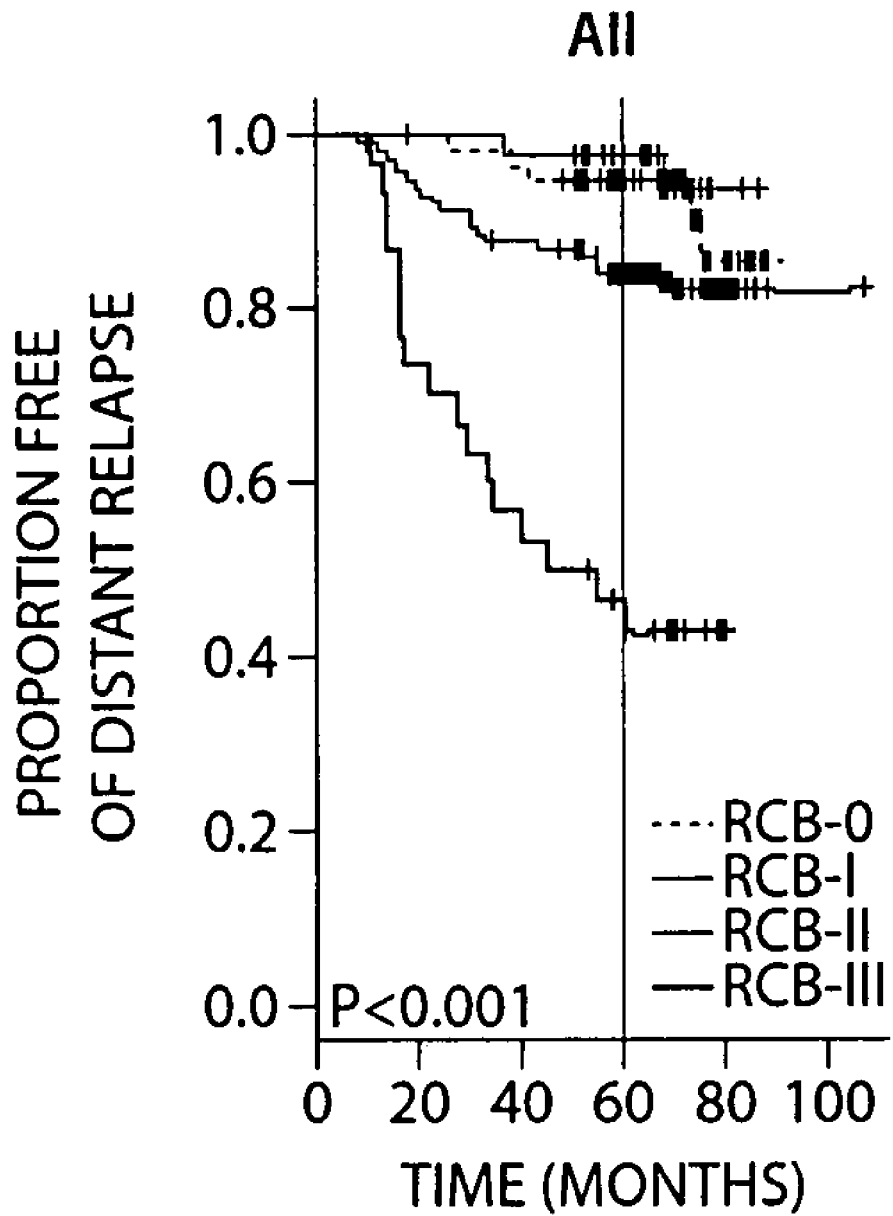
FIGS. 5A-C. Likelihood of distant relapse as a function of residual cancer burden (RCB) group. RCB-0 is equivalent to complete pathologic response (pCR), RCB-I represents minimal residual disease, RCB-II moderate and RCB-III extensive residual disease.
Figure 5B:
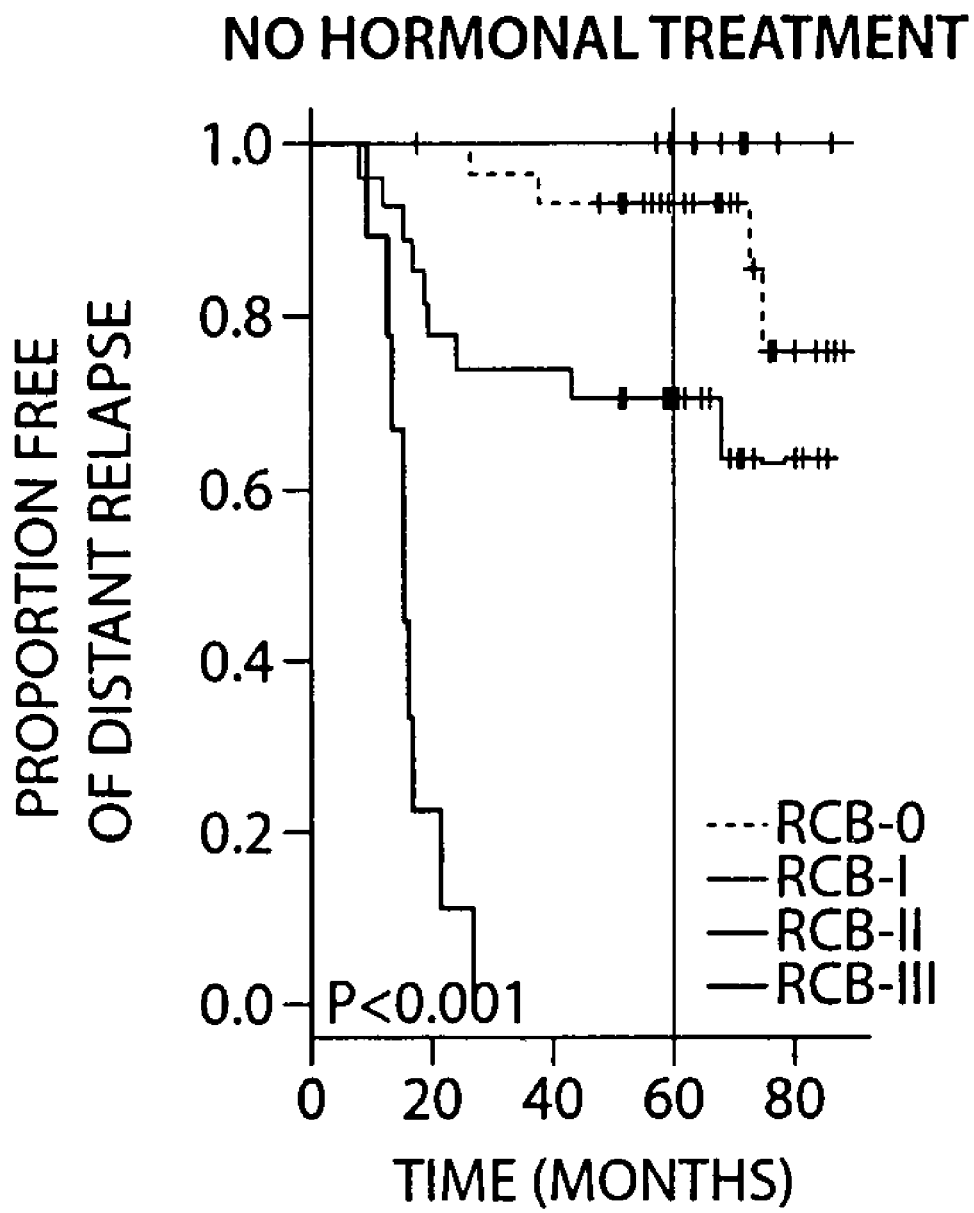
Figure 5C:
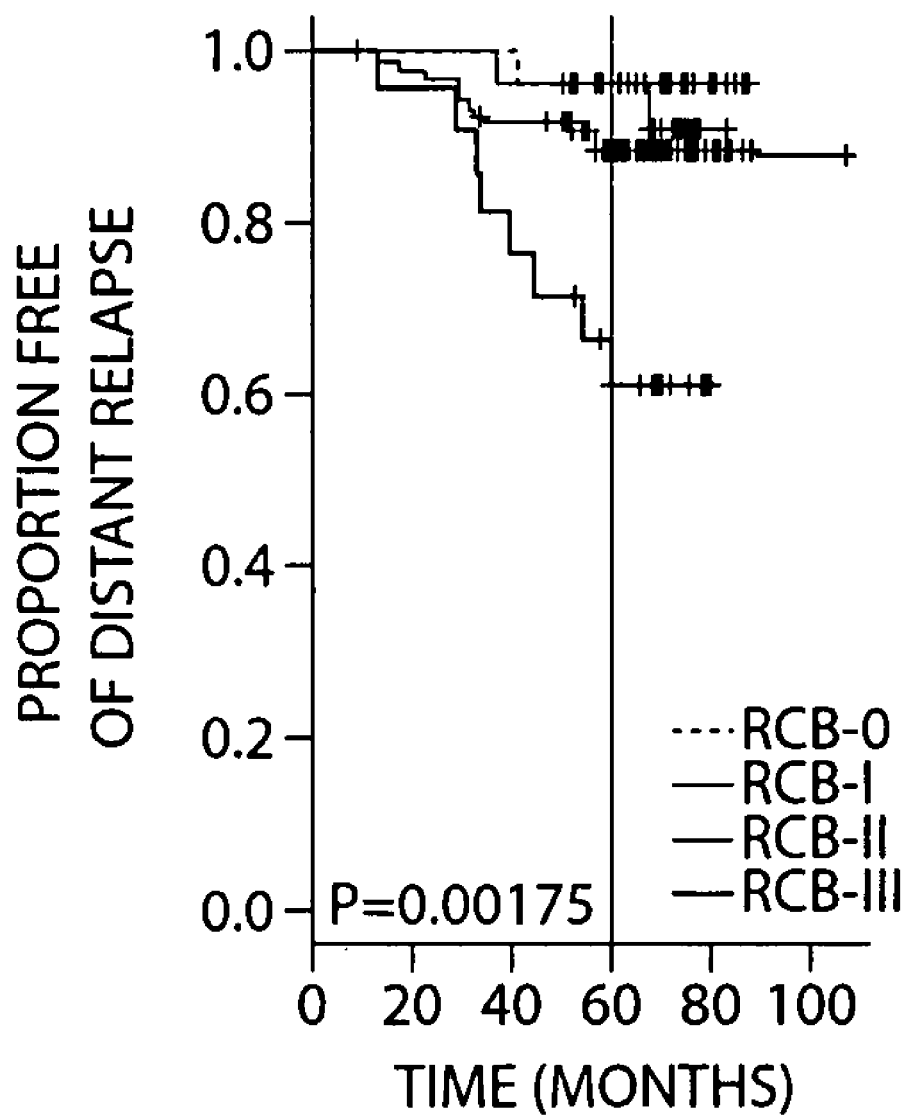

RCB Index Assessment Versus Hormonal Status and AJCC Stage for Predicting Distant Relapse Since adjuvant hormonal therapy likely affects relapse-free survival, we evaluated the risk of relapse within groups who did or did not receive post-surgery hormonal treatment. All hormone receptor (HR) positive patients were eligible for the treatment and 91% of them underwent adjuvant hormonal therapy. Women with RCB-0 and RCB-I after neoadjuvant T/FAC had excellent 5-year relapse-free prognosis irrespective of whether or not they received adjuvant hormonal treatment (FIGS. 5B, 5C). It is noteworthy that nine patients with HR negative breast cancer and RCB-III after neoadjuvant T/FAC chemotherapy all relapsed within 27 months (FIG. 5B). The prognosis of those with RCB-II and RCB-III was markedly improved in the group treated with adjuvant hormonal therapy (FIG. 5C).

Figure 6A:
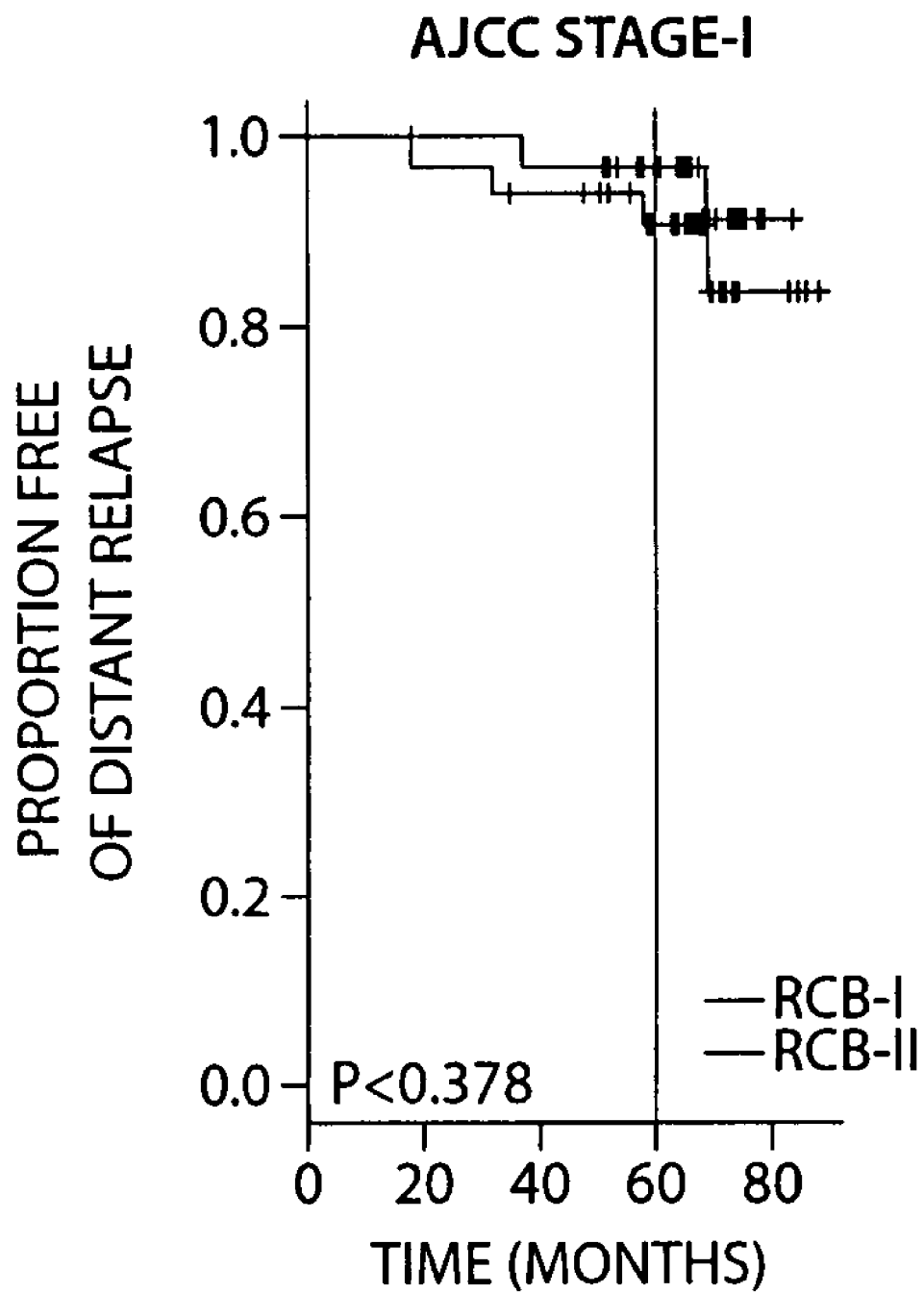
FIGS. 6A-C. Kaplan-Meier distant relapse curves for groups of patients with different AJCC stage after chemotherapy as a function of residual cancer burden (RCB) class.
Figure 6B:
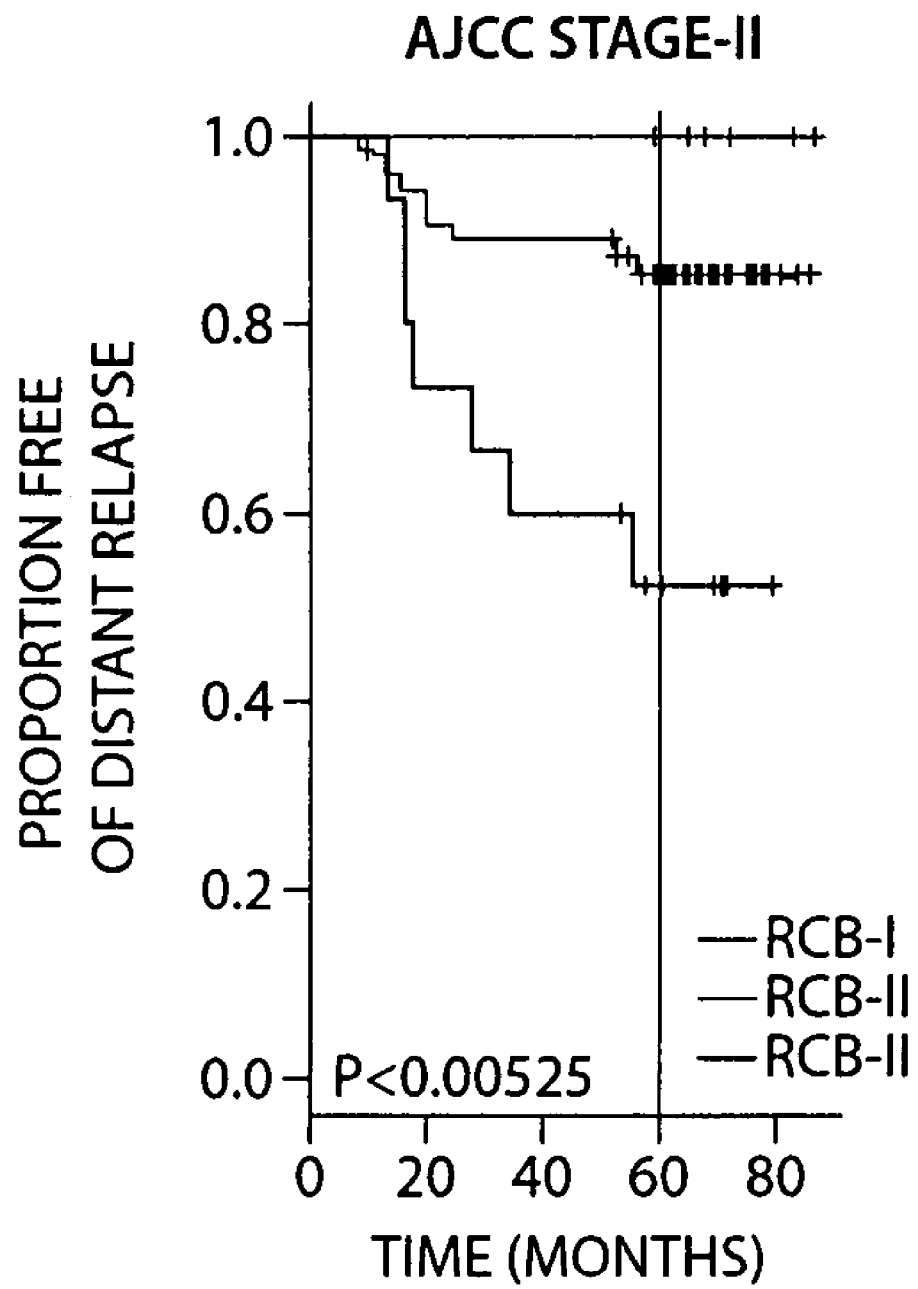
Figure 6C:
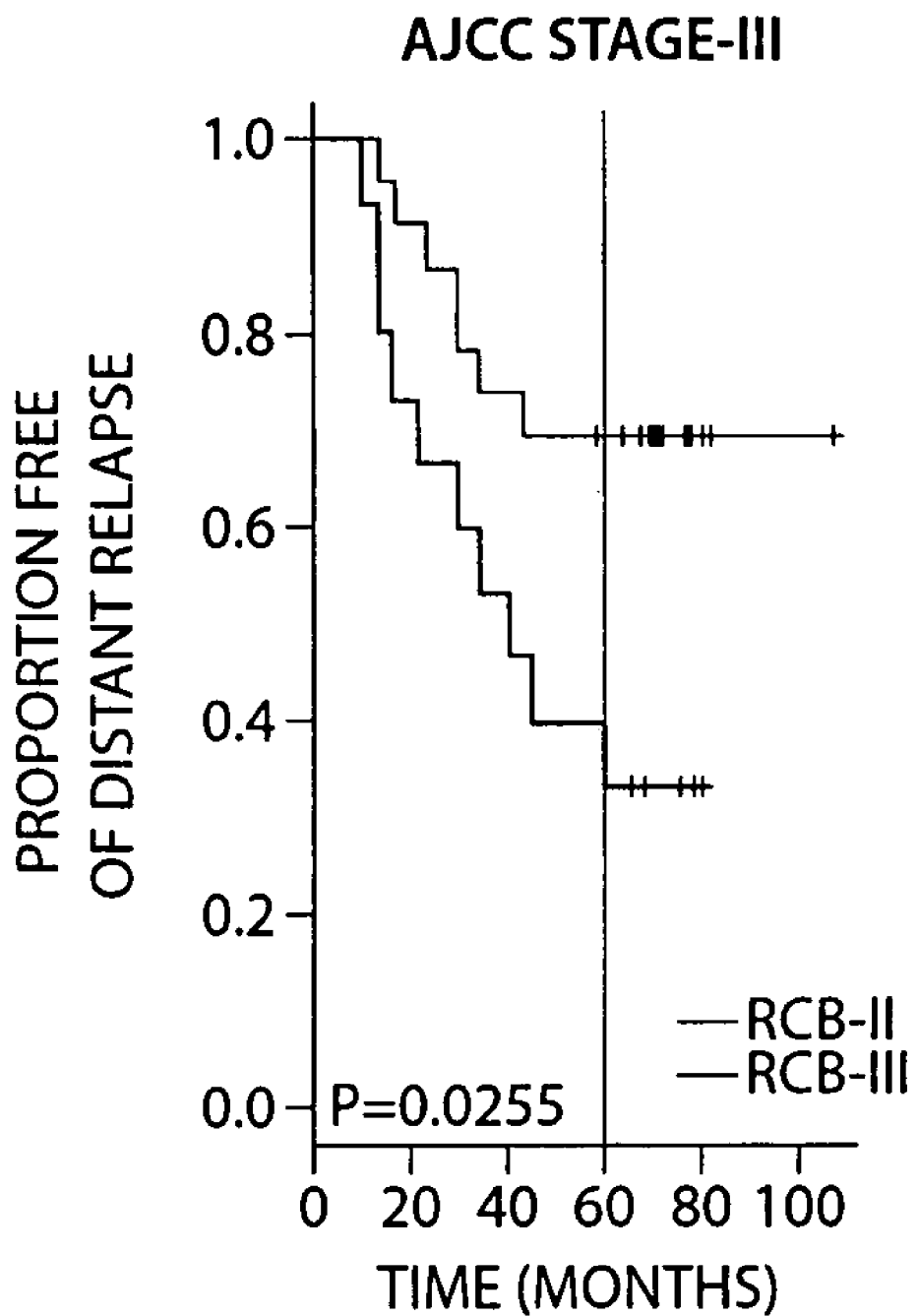
Figure 7A:
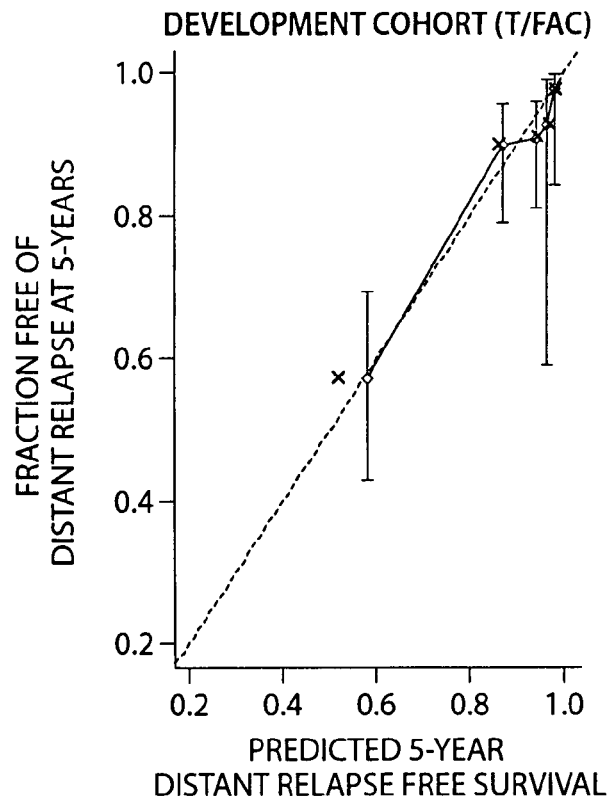
FIGS. 7A-B. Calibration plots of observed versus predicted 5-year distant relapse free survival. Observed rates were obtained from the Kaplan-Meier estimates and predicted rates were from a full multivariate Cox model that contained RCB group and clinical covariates.
Figure 7B:
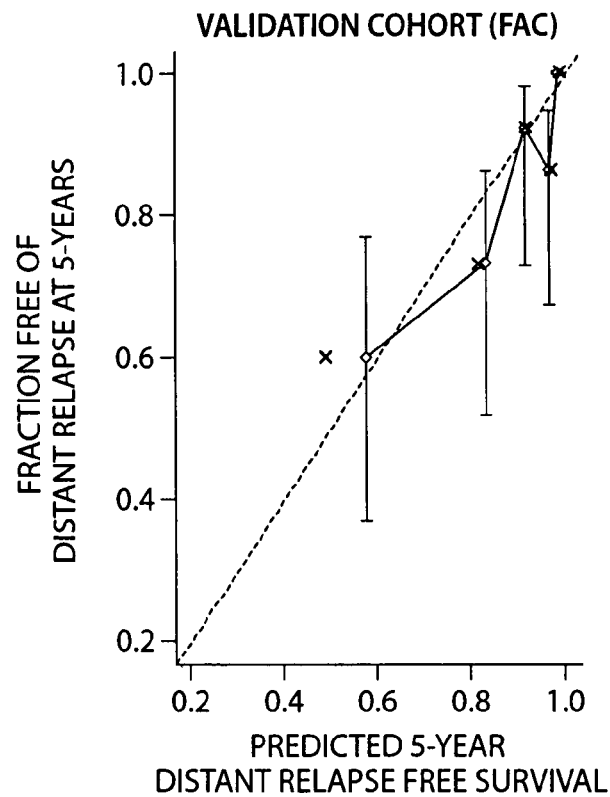

Because tumor size and number of lymph nodes with metastases after chemotherapy are important covariates in the determination of both RCB and AJCC stage, we evaluated whether RCB group adds prognostic information over post-chemotherapy AJCC stage. AJCC stage can effectively separate groups with different prognosis, having an estimated separation in the 5-year rates of distant relapse between Stage-III and Stage-0 patients of 36.6% (95% CI 3.2-74.7), which is comparable to the separation provided by RCB groups. To evaluate the contribution of the RCB group to the prognostic power of post-therapy AJCC stage, we examined the Kaplan-Meier estimates of distant relapse within each AJCC stage group (FIG. 6) (Simon, 2005) Of course, RCB-0 and Stage 0 both identify those with pathologic complete response (pCR). RCB did not add significant prognostic information for Stage I patients (P=0.38; FIG. 7A), but RCB classified Stage II patients in three subgroups (P=0.005; FIG. 7B) and Stage III patients in two subgroups (P=0.025; FIG. 7C) with significantly different prognoses. Therefore, RCB classification appears to add significant prognostic power compared to post-treatment pathologic AJCC stage, at least for Stage II/III tumors that represent 48% of the T/FAC treated cohort.

Example 5

Validating RCB Index

Applying RCB Classification to Analyze an Independent FAC Study

We assessed the accuracy of RCB as predictor of distant relapse in the T/FAC-treated cohort and also its generalizability, i.e. the ability to accurately predict the relapse probabilities in an independent cohort of 141 patients treated with neoadjuvant FAC (Kattan, 2003; Simon, 2005; Justice et al., 1999).

Figure 8A:
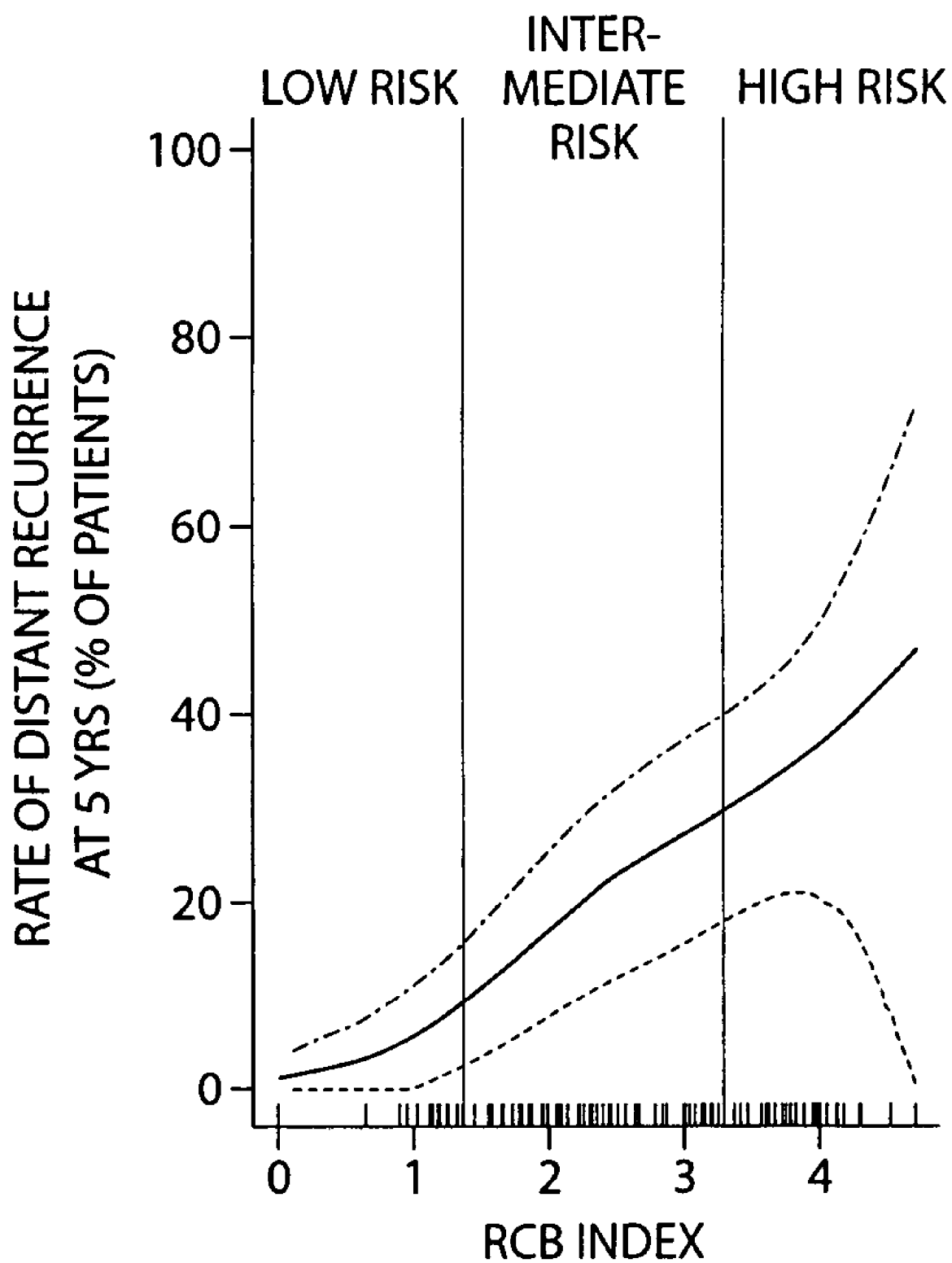
FIGS. 8A-B. Likelihood of 5-year Distant Relapse as a Continuous Function of RCB Estimated from the Patient Cohort that Received Neoadjuvant FAC chemotherapy.

We first evaluated the intrinsic prognostic accuracy of the RCB-based survival model by comparing the predicted probabilities of distant relapse at 5 years produced by the full multivariate Cox regression model that included RCB group and the clinical covariates to the observed probabilities (Justice et al., 1999) The calibration plot suggests that the probabilities of distant relapse predicted by the RCB survival model are similar to the empirical Kaplan-Meier estimates within the 5 groups defined by the quintiles of the distribution of predicted survival (FIG. 8A; cross symbols). We used bootstrap resampling to evaluate potential overoptimism in the predictions of RCB prognostic model, which refers to the bias introduced by "using the data twice", that is for selecting cut points and also for evaluating the model's predictive accuracy (Schumacher et al., 1997; Harrell, 2001). The estimated global shrinkage factor of 0.871 indicated only moderate overfitting (a shrinkage factor of 1 indicates no overfitting). The prognostic model was adjusted by multiplying the linear risk predictor of the Cox model by the above shrinkage factor, and its calibration is shown in FIG. 5A (filled symbols). The optimism-adjusted model appears to predict accurately the relapse-free rates at 5 years in the T/FAC cohort.

Another measure of intrinsic prognostic ability of the RCB-based model is its discrimination, which is defined as the ability to distinguish higher and lower risk patients (Justice, 1999). A measure of discrimination is Harrell's c-index, which is a generalization of the area under the receiver operating characteristic (ROC) curve for censored observations: it is the probability of concordance between observed and predicted survival in pairs of individuals (c=0.5 for random predictions, c=1 for perfectly discriminating model) (Harrell, 2001). The bias-adjusted c-index in the development cohort was estimated by bootstrap resampling to be 0.77 (95% CI 0.69-0.84) indicating sufficient discrimination.

Figure 8B:
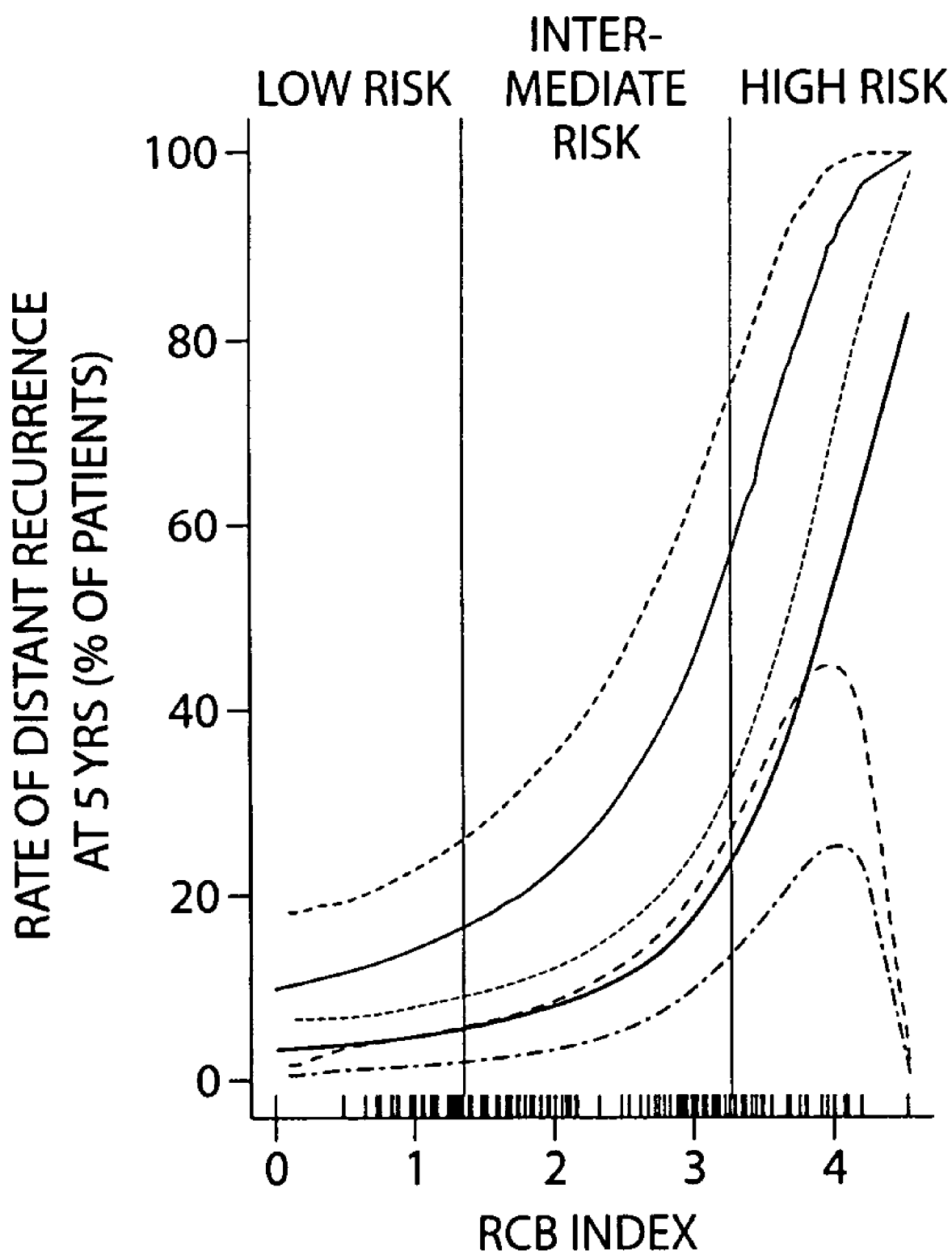

To evaluate the generalizability of the RCB system we evaluated the accuracy of its relapse predictions on an independent cohort of patients that were treated with neoadjuvant FAC chemotherapy. The same RCB cut points defined groups with increasingly poor 5-year and 10-year prognoses in the validation cohort of FAC treated patients (Table 4). The difference in the rates of distant relapse between the worst (RCB-III) and best (RCB-0) prognosis groups was 36.8% (95% CI 18.2-55.5) at 5 years and 31.4% (95% CI 0.1-78.4) at 10 years. The separation of the 5-year relapse rates is smaller than that for the T/FAC cohort (48.1%), indicating some optimism in those predictions. We then applied the shrunken multivariate Cox model to predict the probabilities of distant relapse for patients in the FAC-treated cohort. The calibration plot for the unadjusted and shrunken models is shown in FIG. 8B. Although the agreement with the observed rates was not as good as that for the T/FAC group, no systematic bias was apparent, especially for the optimism-adjusted model. Therefore we can conclude that the model based on the RCB system and clinical covariates can accurately predict the probability of distant relapse in an independent cohort of patients that were treated with a different chemotherapy regimen. Furthermore, the c-index of the prognostic model on the validation cohort was 0.70 (95% CI 0.61-0.79), which although slightly lower than the index estimated in the development cohort, suggests similar discriminatory ability. Taken together, these results validate the prognostic ability of the RCB system for predicting distant relapse in breast cancer patients treated with neoadjuvant T/FAC or FAC chemotherapy.

Figure 9A:
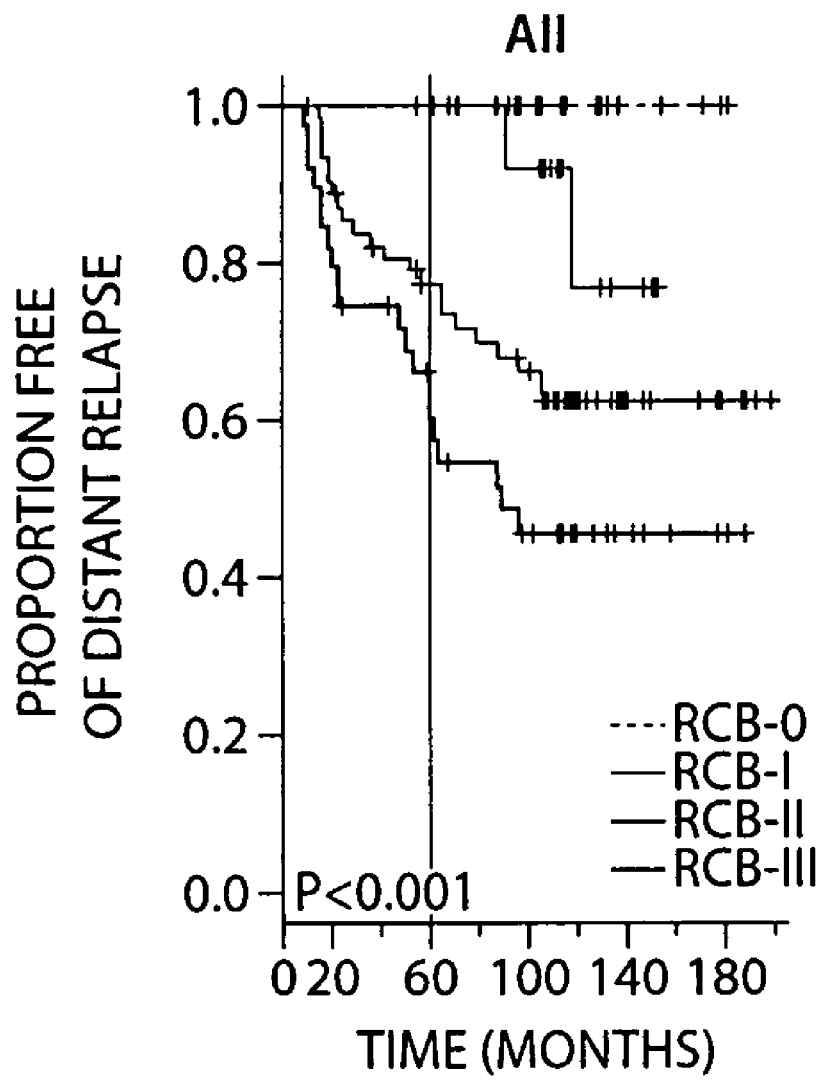
FIGS. 9A-C. Likelihood of distant relapse as a function of residual cancer burden (RCB) group in FAC-treated patients.
Figure 9B:
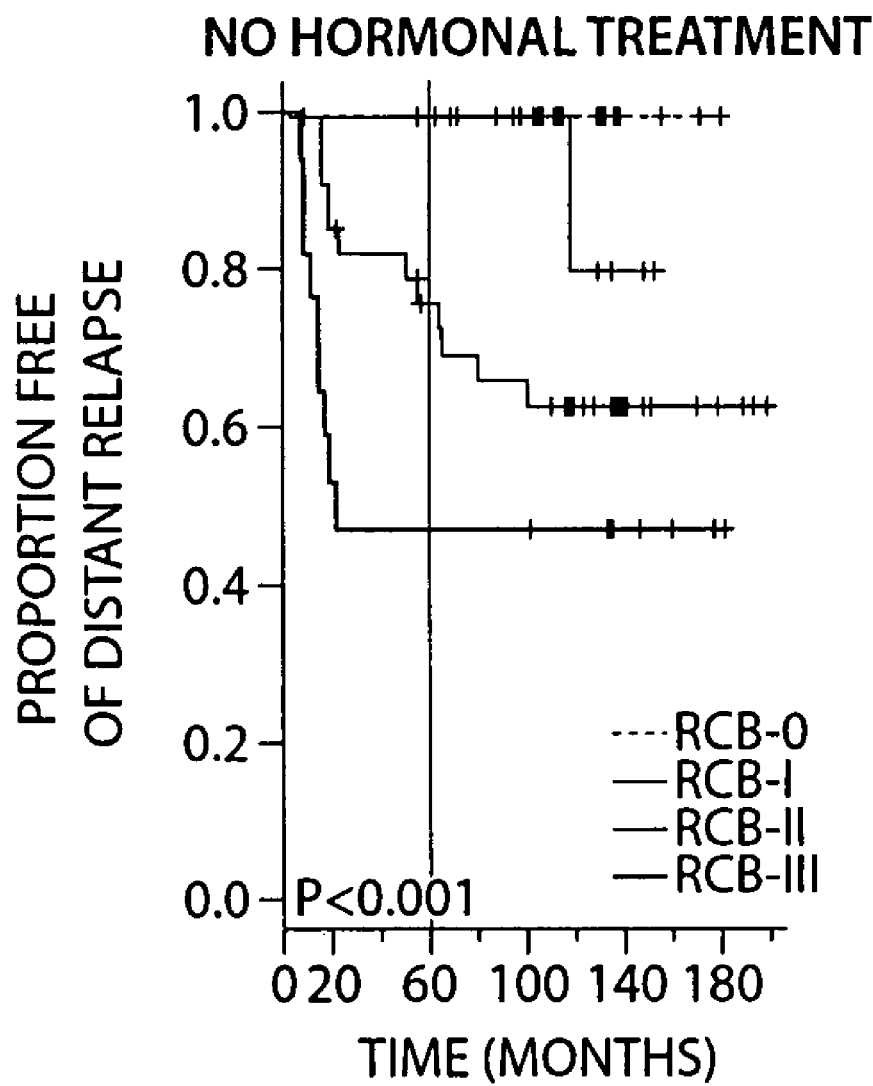
Figure 9C:
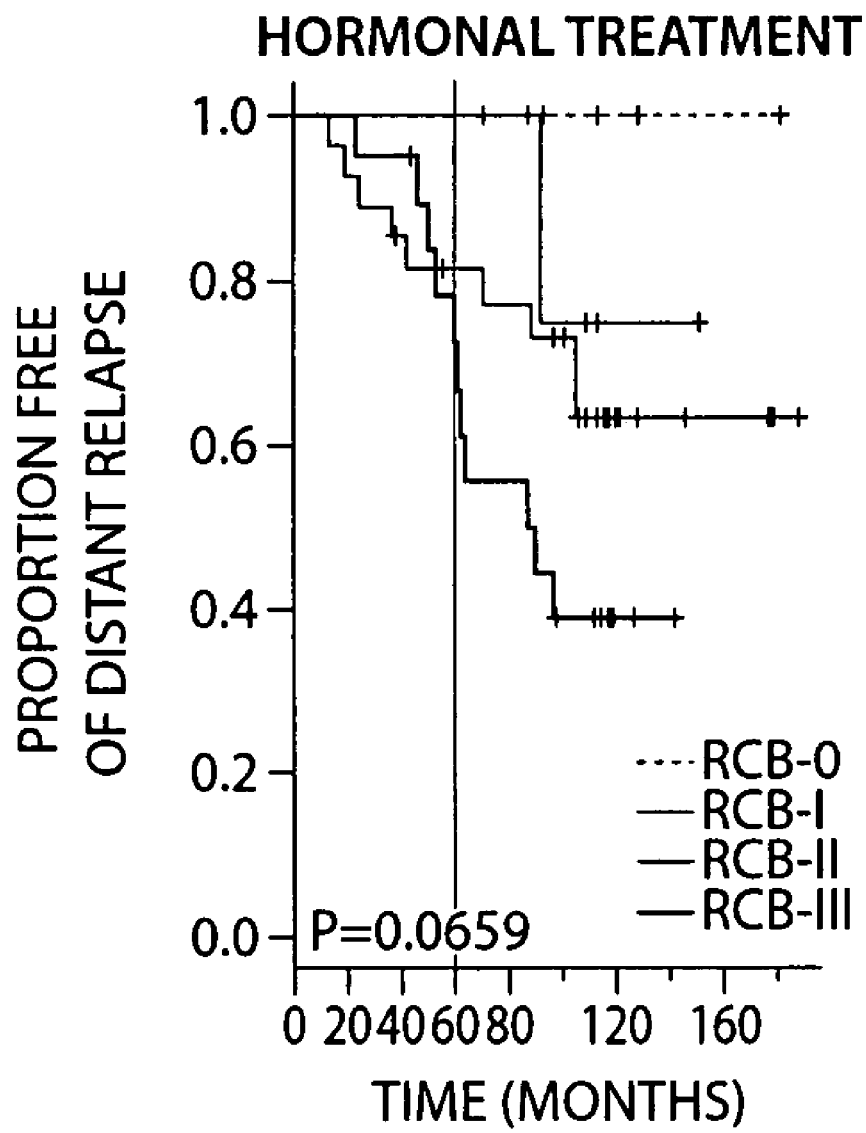
Figure 10A:
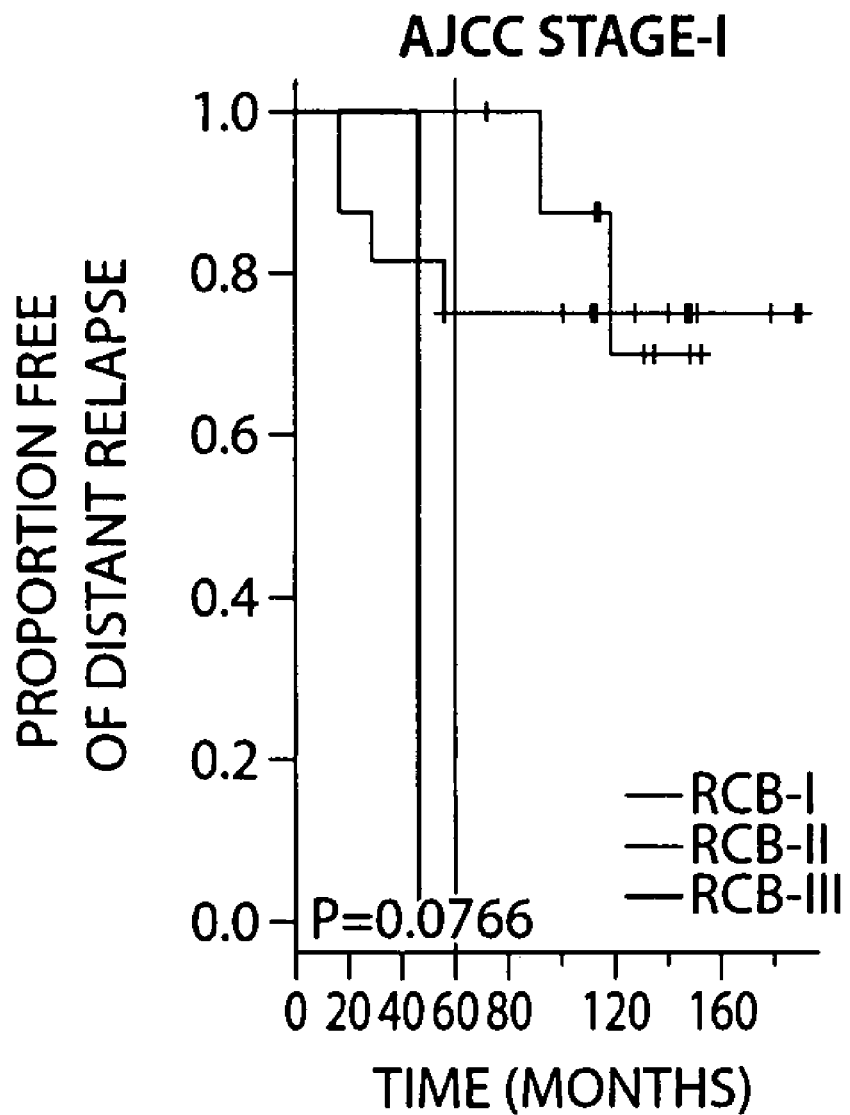
FIGS. 10A-C. Kaplan-Meier distant relapse curves for groups of patients with different AJCC stage after FAC chemotherapy as a function of residual cancer burden (RCB) class.
Figure 10B:
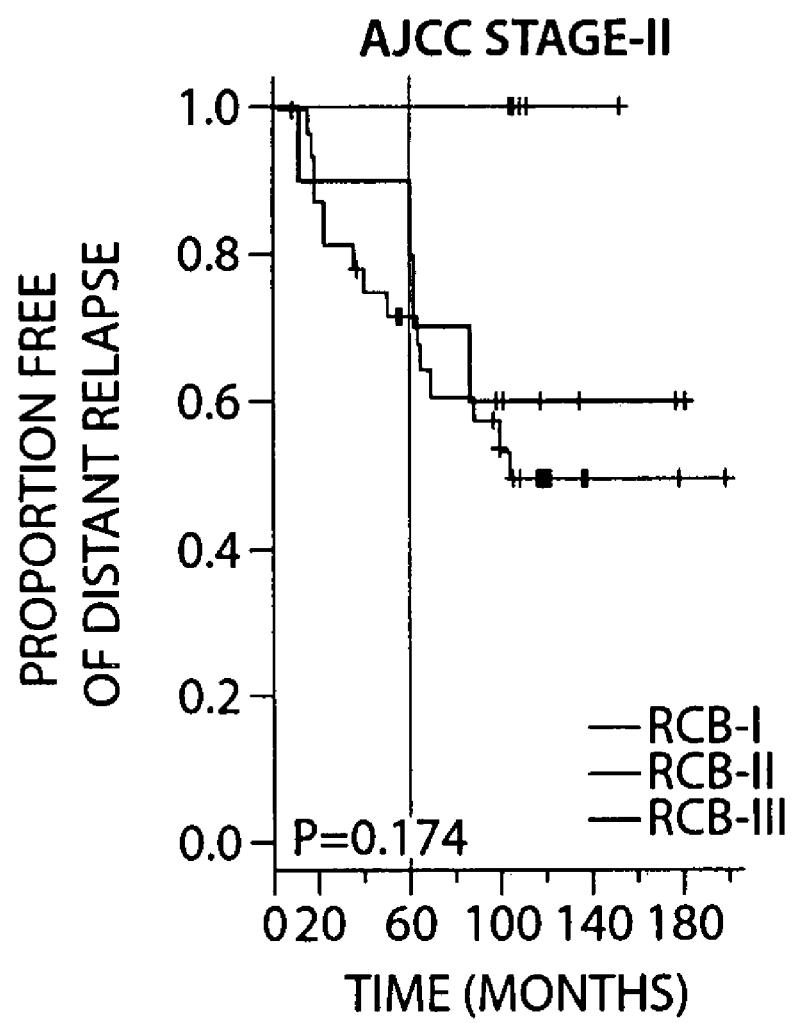
Figure 10C:
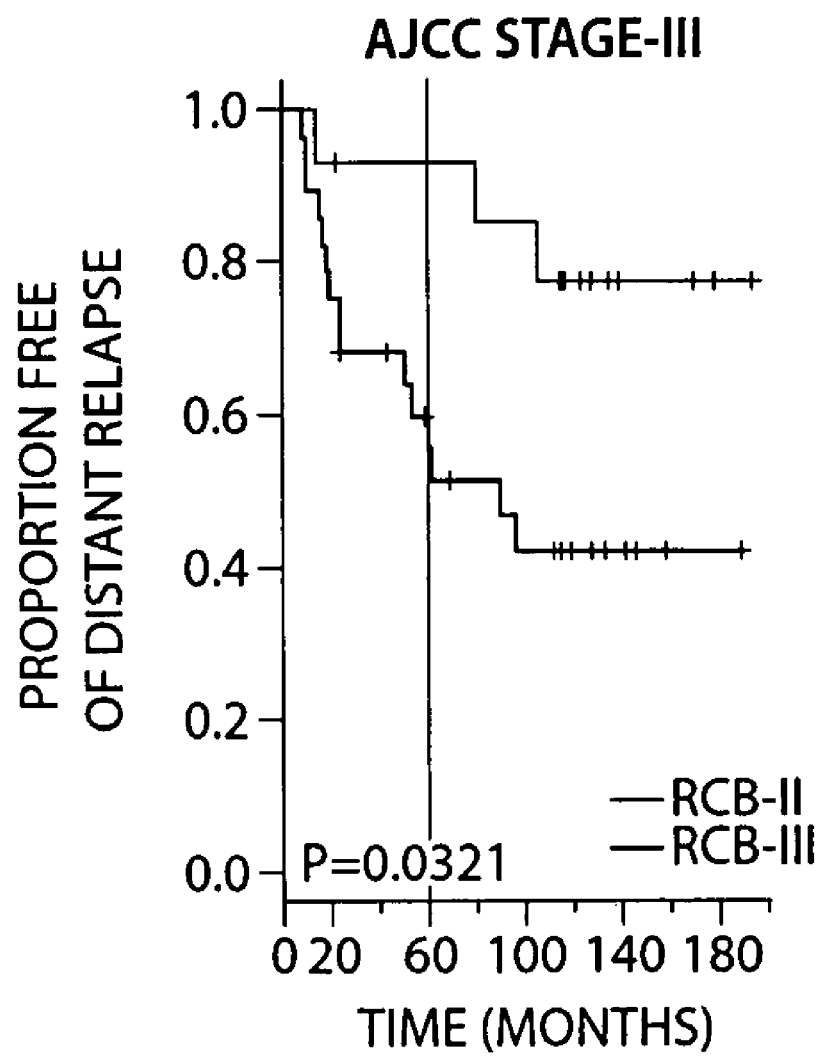

Other analyses of the FAC-treated cohort showed trends consistent with those observed with TFAC patients. FIG. 8 shows the likelihood of 5-year distant relapse as a continuous function of RCB estimated from the patient cohort that received neoadjuvant FAC chemotherapy. FIG. 9 shows the effect of hormonal status and treatment on RCB classes in FAC-treated patients. FIG. 10 shows the AJCC Stage effect on RCB classes in FAC-treated patients.

Example 6

RCB Classification and Nodal Status

Figure 11A:
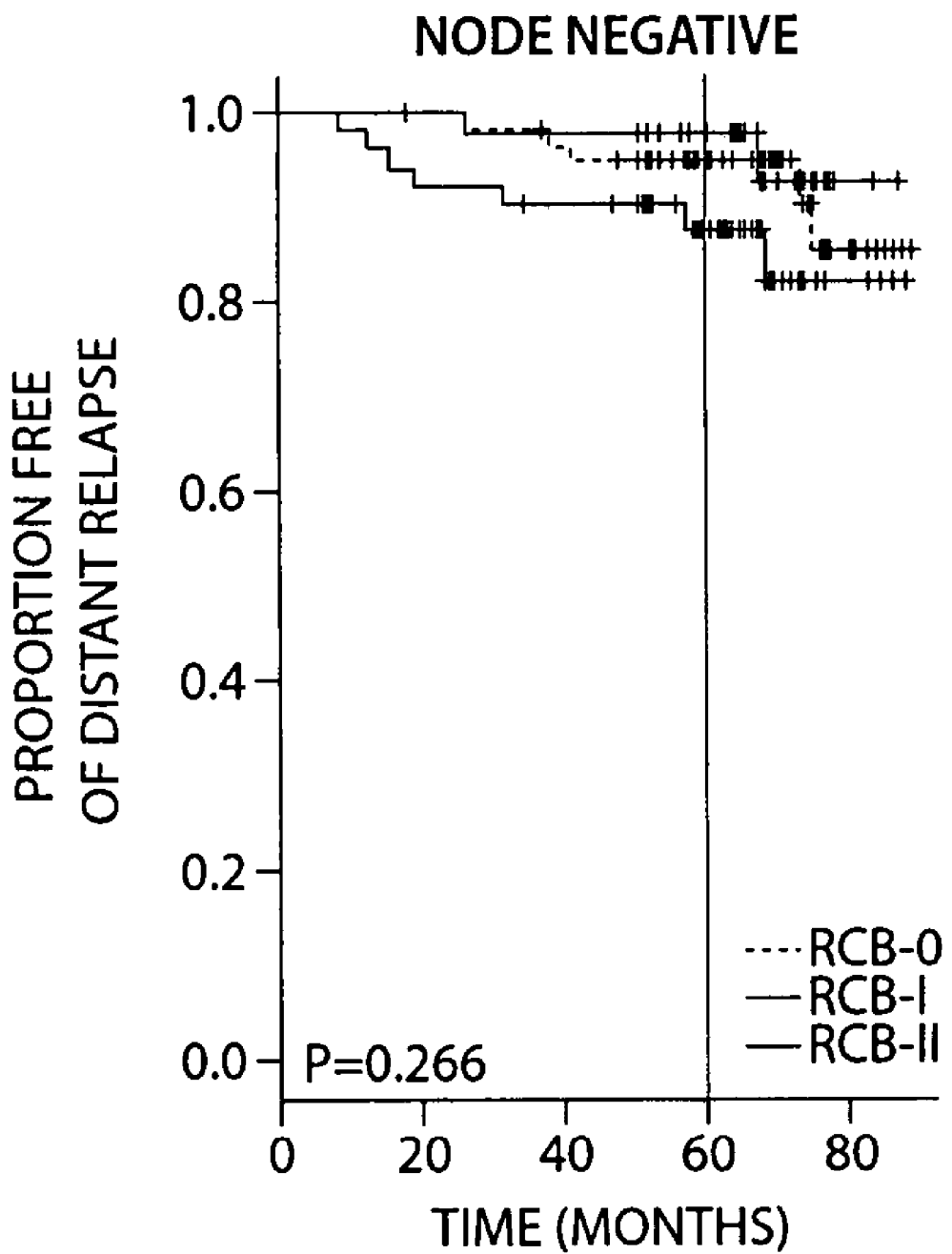
FIG. 11. Likelihood of distant relapse by post-surgery nodal status in the T/FAC treated cohort as a function of residual cancer burden (RCB) group. The RCB group does not provide significant stratification of relapse risk among node-negative patients, but among the node-positive it does identify 6 patients with minimal residual disease and excellent prognosis (RCB-I) and 30 patients with extensive residual disease and poor relapse prognosis (RCB-III).
Figure 11B:
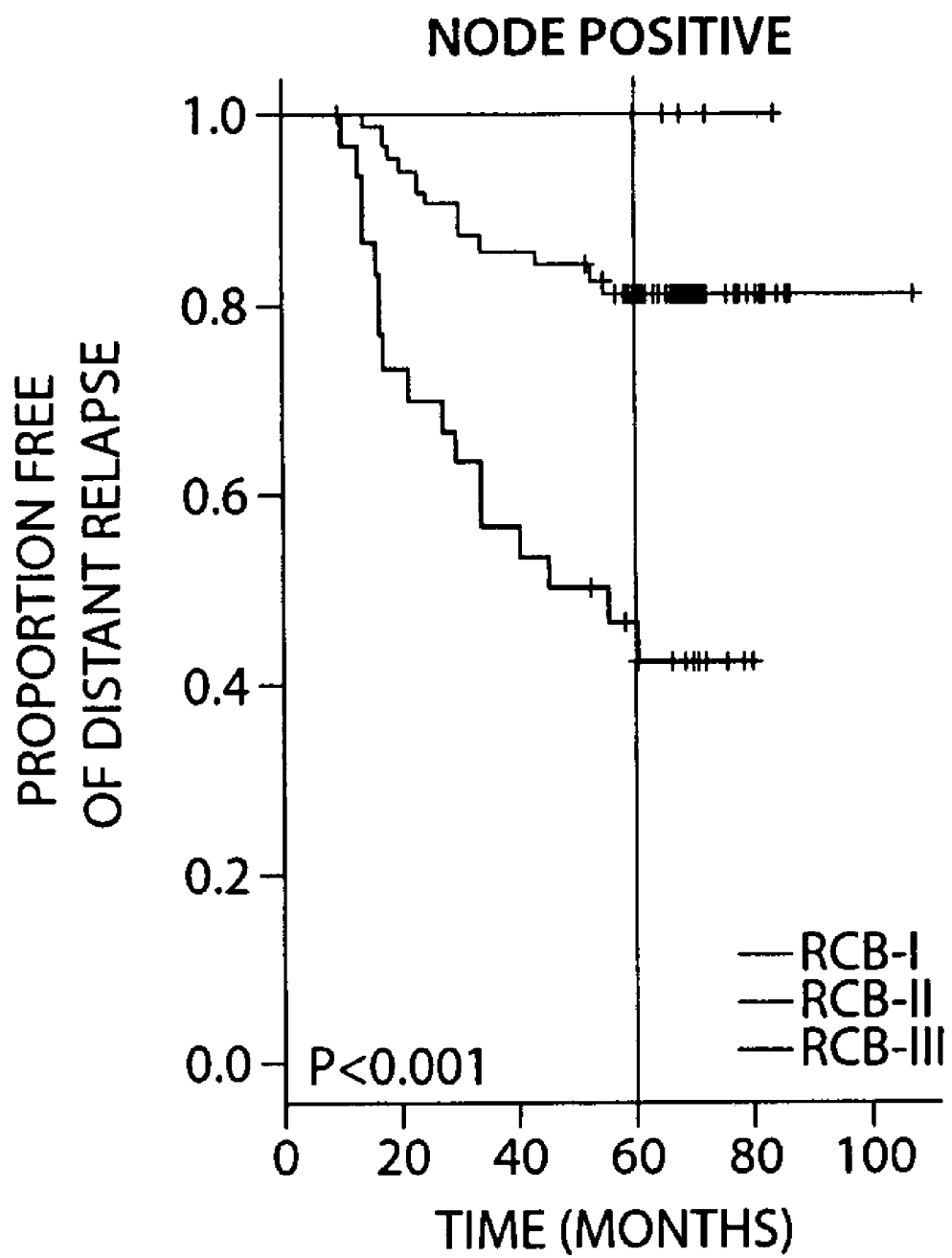
Figure 12A:
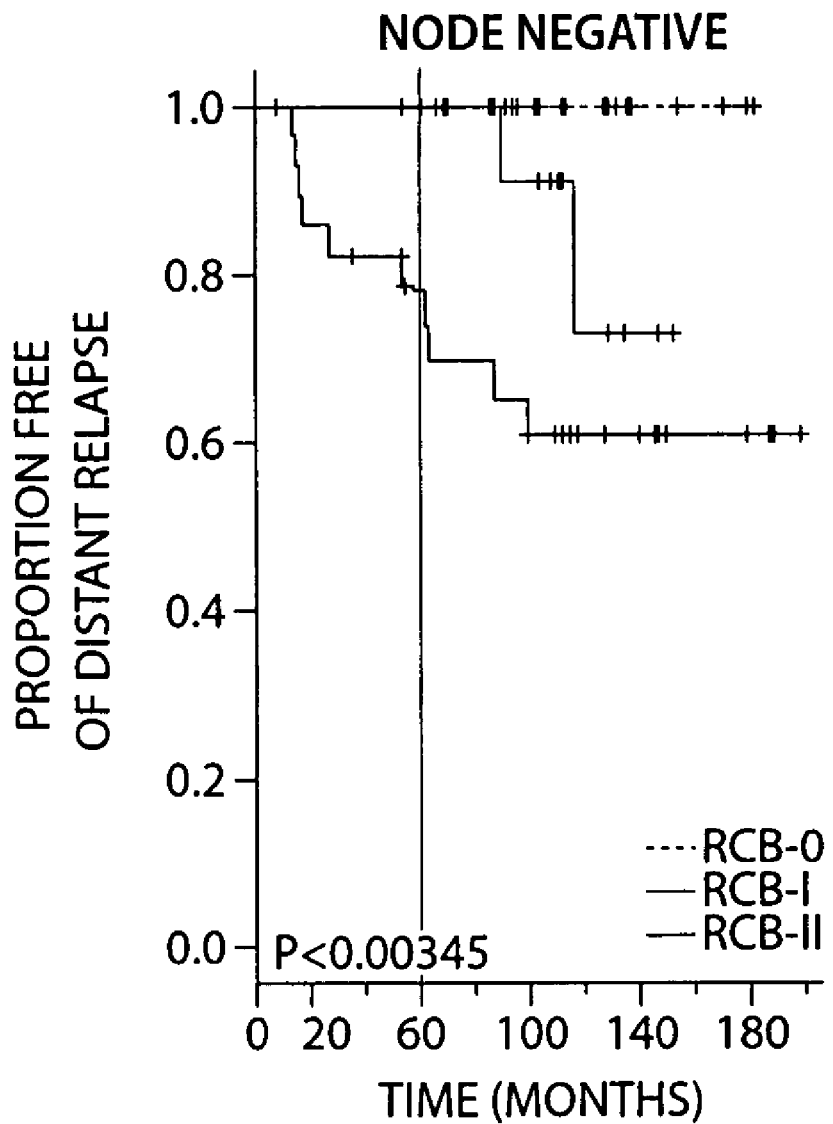
FIG. 12. Likelihood of distant relapse by post-surgery nodal status in the FAC treated cohort as a function of residual cancer burden (RCB) group.
Figure 12B:
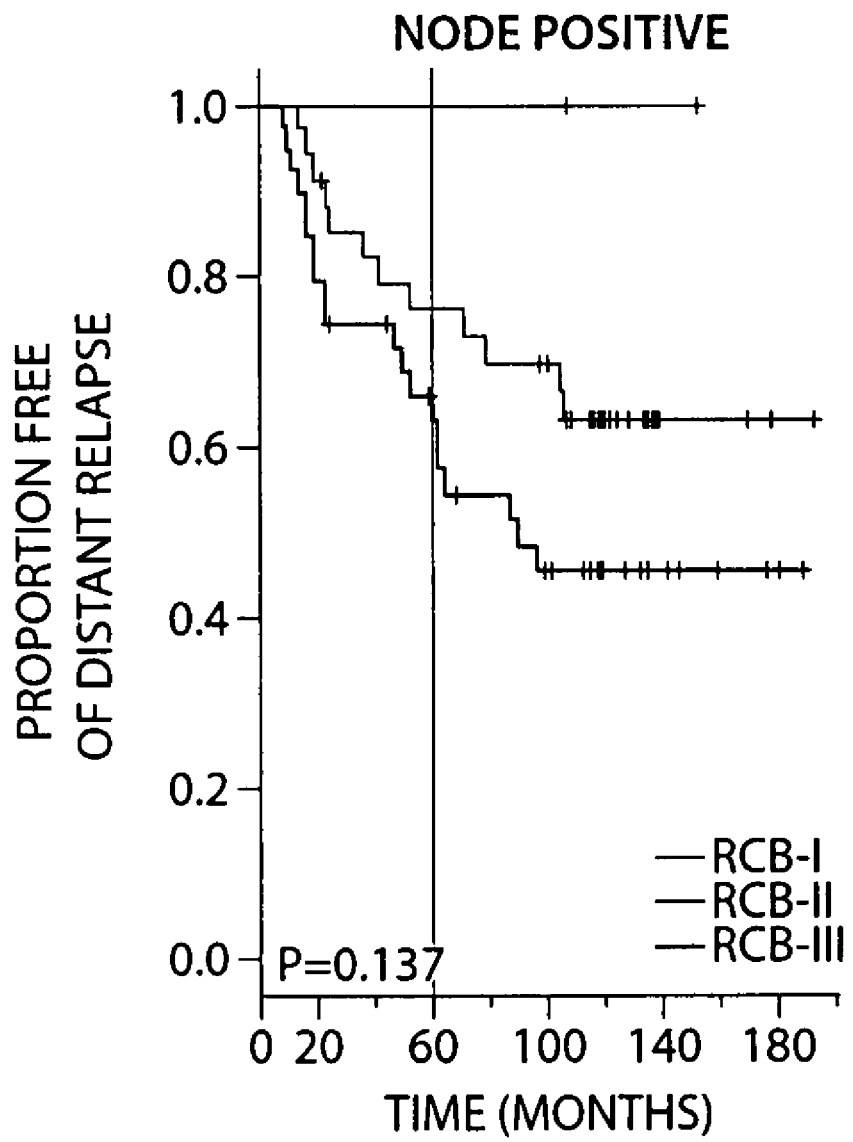

The likelihood of distant relapse by post-surgery nodal status in the T/FAC treated cohort as a function of residual cancer burden (RCB) group is described in FIG. 11. The RCB group does not provide significant stratification of relapse risk among node-negative patients, but among the node-positive it does identify 6 patients with minimal residual disease and excellent prognosis (RCB-I) and 30 patients with extensive residual disease and poor relapse prognosis (RCB-III). A similar analysis for FAC-treated patients is shown in FIG. 12.

Example 7

Characterization of Primary and Metastatic Terms in RCB Index

Figure 13:
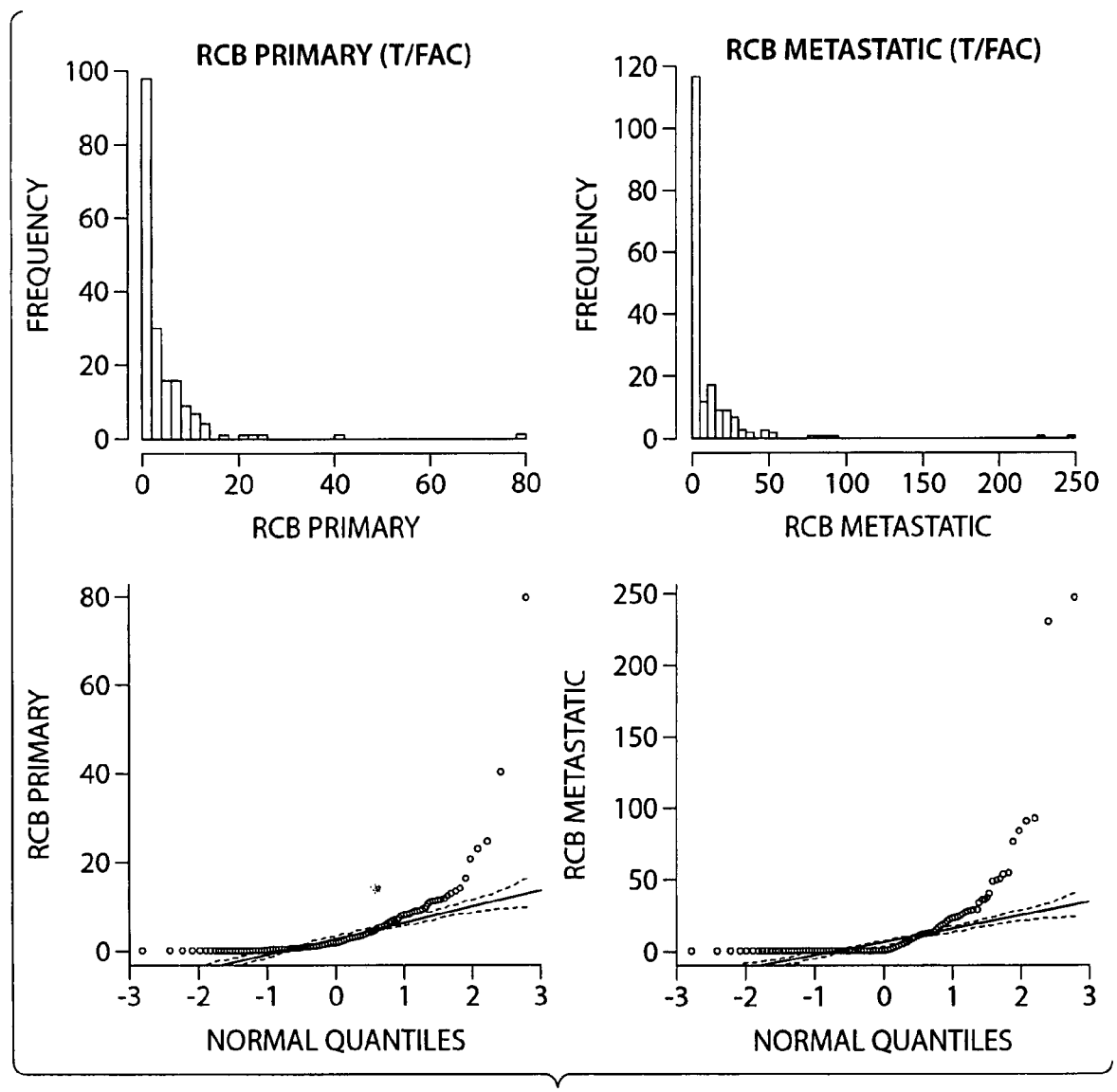
FIG. 13. Distribution of untransformed terms for primary (left) and metastatic (right) contributions to the RCB index. The histograms at the top show that the distributions are highly skewed. The normal quantile plots at the bottom show the severe deviations from normality. Data are from the T/FAC treated cohort with residual disease (RCB>0).
Figure 14:
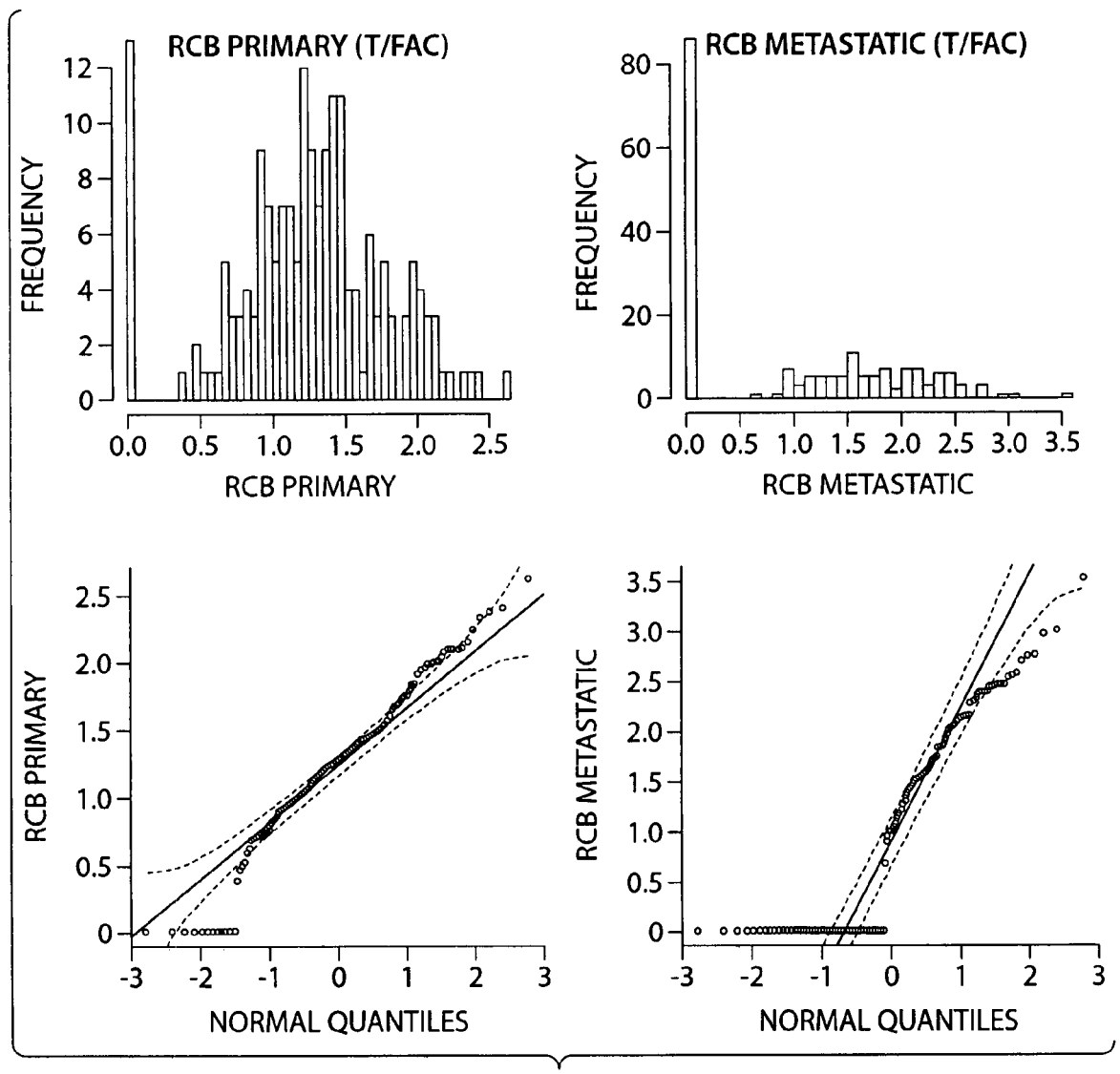
FIG. 14. Distribution of for primary (left) and metastatic (right) RCB terms after transformation. The distributions are considerably more symmetric and closer to normality. Data are from the T/FAC treated cohort with residual disease (RCB>0).
Figure 15:
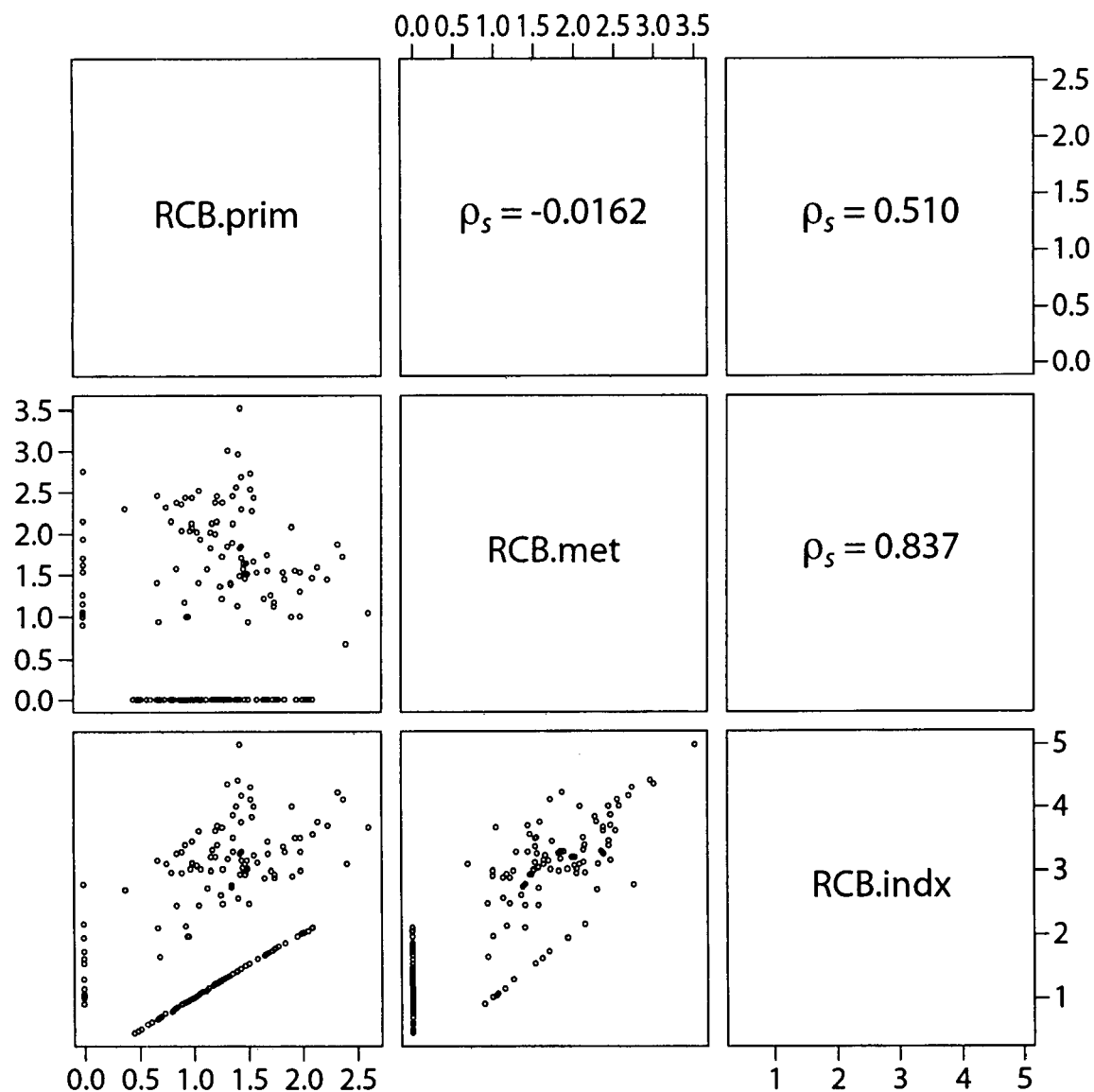
FIG. 15. Scatter plots and pair-wise Spearman-rank correlations between the transformed primary and metastatic RCB components and the combined RCB index. The correlation between the primary and metastatic components is negligible, suggesting that the primary and metastatic terms provide independent information on the residual disease. The combined RCB index appears to be correlated more strongly with the metastatic term ($\rho_s=0.837$) compared to the primary term ($\rho_s=0.510$). Data are from the T/FAC treated cohort.
Figure 16A:
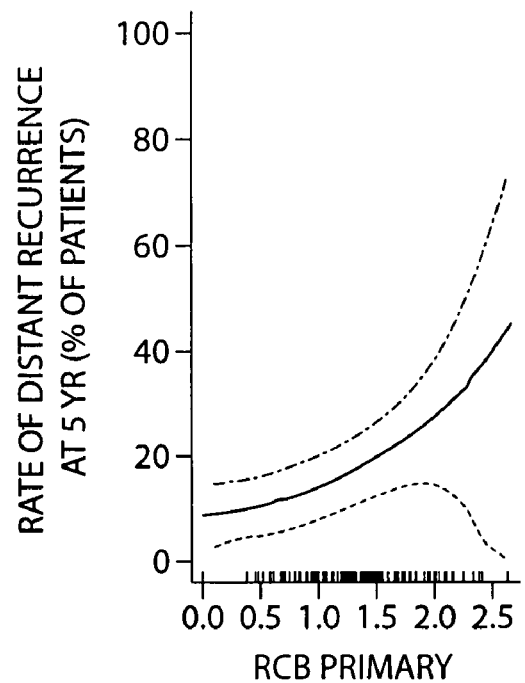
FIG. 16. Distant relapse risk at 5 years as a function of the primary and metastatic terms of the RCB index. These risk curves were produced by univariate Cox regression models and therefore are adjusted for the effects of other clinical covariates. See the statistical methods and FIG. 2 for further details. Both terms are predictive of risk, with the primary term dominating the lower range of the index and the metastatic term dominating the upper range of the combined RCB index.
Figure 16B:
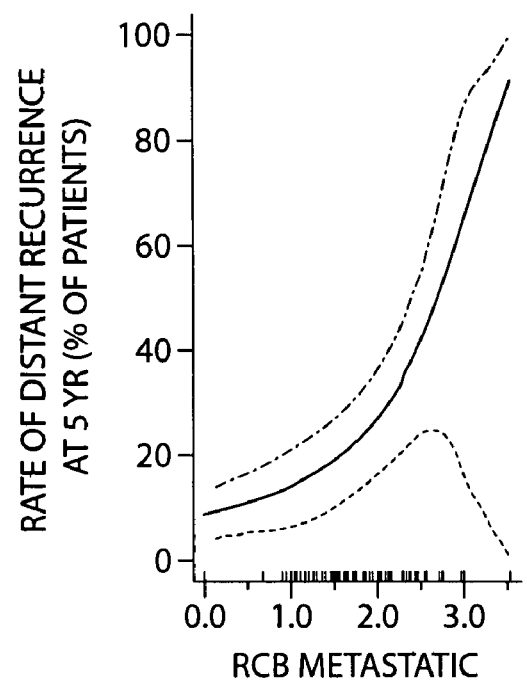
Figure 16C:
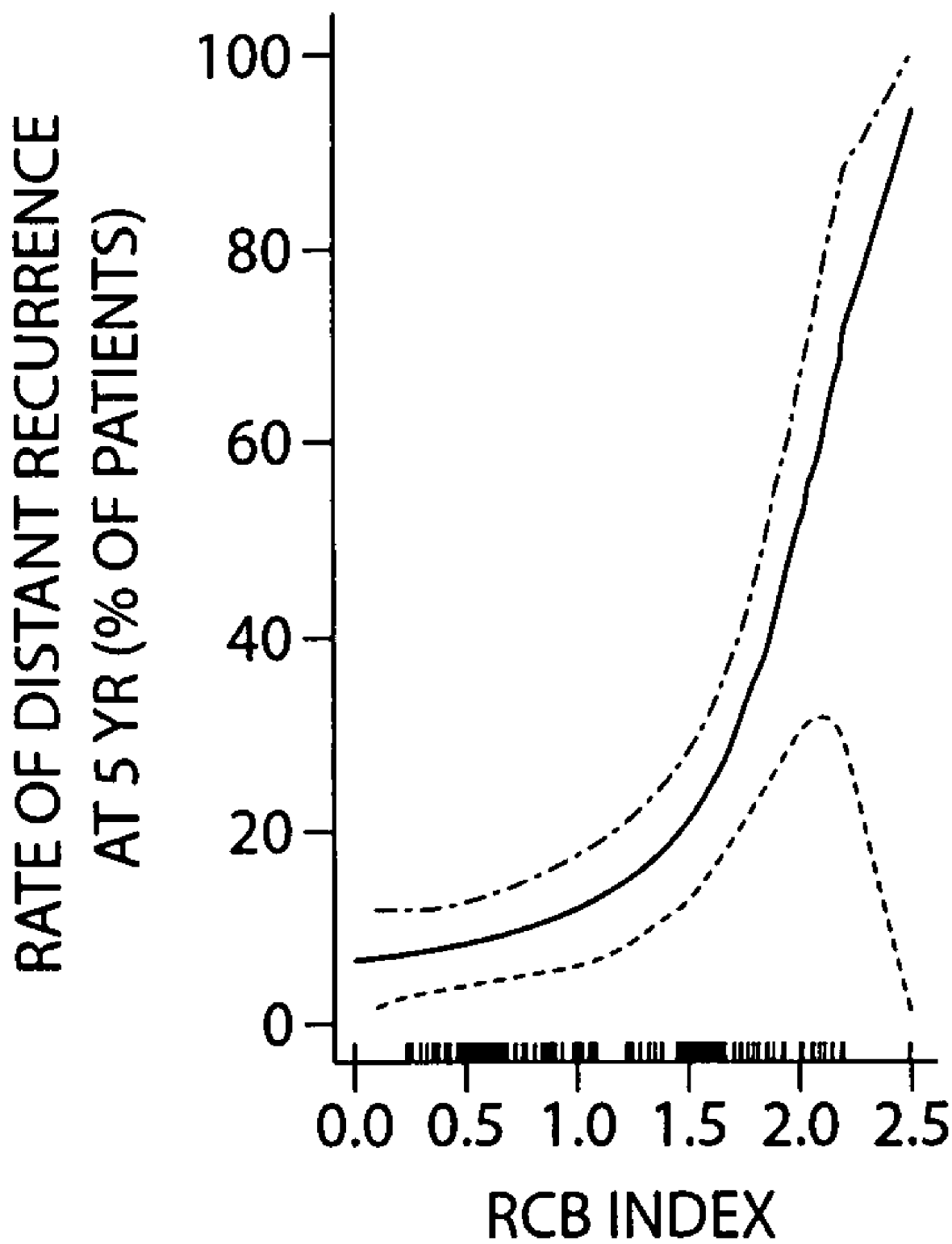

FIG. 13. shows the distribution of untransformed terms for primary (left) and metastatic (right) contributions to the RCB index. The histograms at the top show that the distributions are highly skewed. The normal quantile plots at the bottom show the severe deviations from normality. Data are from the T/FAC treated cohort with residual disease (RCB>0). FIG. 14. is the distribution of for primary (left) and metastatic (right) RCB terms after transformation. The distributions are considerably more symmetric and closer to normality. Data are also from the T/FAC treated cohort with residual disease (RCB>0). FIG. 15 shows scatter plots and pair-wise Spearman-rank correlations between the transformed primary and metastatic RCB components and the combined RCB index. The correlation between the primary and metastatic components is negligible, suggesting that the primary and metastatic terms provide independent information on the residual disease. The combined RCB index appears to be correlated more strongly with the metastatic term ($\rho_s$=0.837) compared to the primary term ($\rho_s$=0.510). Data are from the T/FAC treated cohort. FIG. 16 shows the distant relapse risk at 5 years as a function of the primary and metastatic terms of the RCB index. These risk curves were produced by univariate Cox regression models and therefore are adjusted for the effects of other clinical covariates. Both terms are predictive of risk, with the primary term dominating the lower range of the index and the metastatic term dominating the upper range of the combined RCB index.

Example 8

Alternate Definitions of RCB Index

1. Base Definitions of an RCB Index

The pathologic measurements in principle can be combined to form an index of residual disease based on contributions from the primary tumor bed and from metastases to lymph nodes. Therefore a formula for an index of Residual Cancer Burden can be stated as follows:

$$RCB = RCB_{PRIM} + RCB_{MET} \quad (3)$$
$$= f_{cell} A_{PRIM} + (LN) A_{MET},$$

where A represents the total area of primary tumor or metastases and the other symbols are as defined in Eq. (1). The primary tumor area can be estimated from the product of the bidimensional diameters of the primary tumor bed in the resection specimen ($d_1$ and $d_2$). Similarly, the metastatic area can be estimated from the size of the largest metastasis ($d_{met}$). Therefore a simple definition of an RCB index is:

$$RCB^{(0)} = f_{cell}(d_1 d_2) + 0.5(LN)d_{met}^2, \quad (4)$$

Figure 17A:
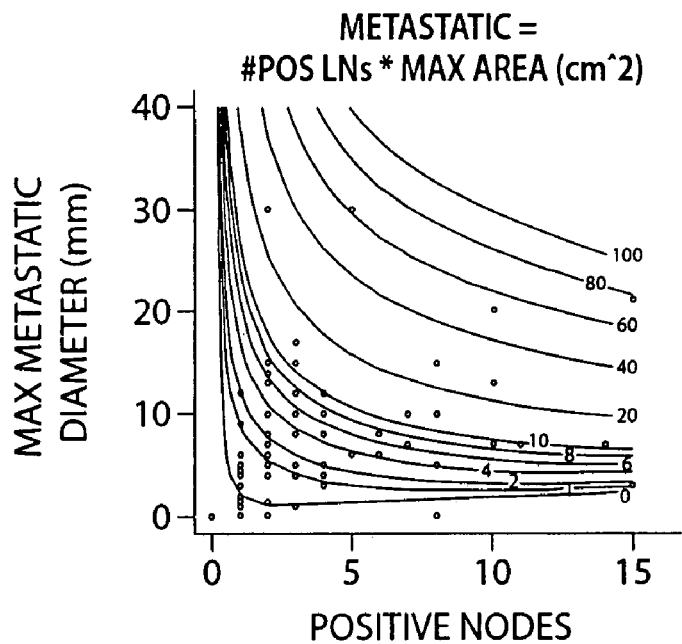
FIGS. 17A-F are graphs showing the effect of the number of positive lymph nodes and of the size of the largest nodal metastasis on the metastatic RCB risk for the six different models. The contours show combinations of the two variables that result in the same contribution to RCB.
Figure 17B:
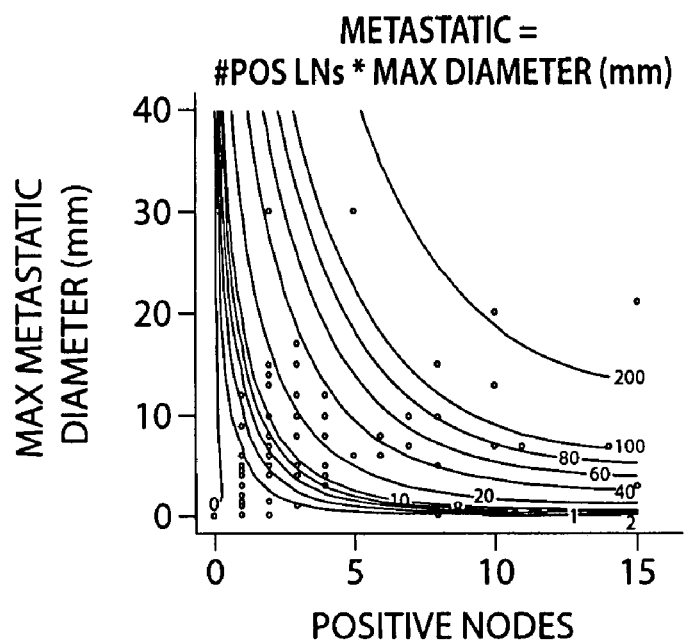
Figure 17C:
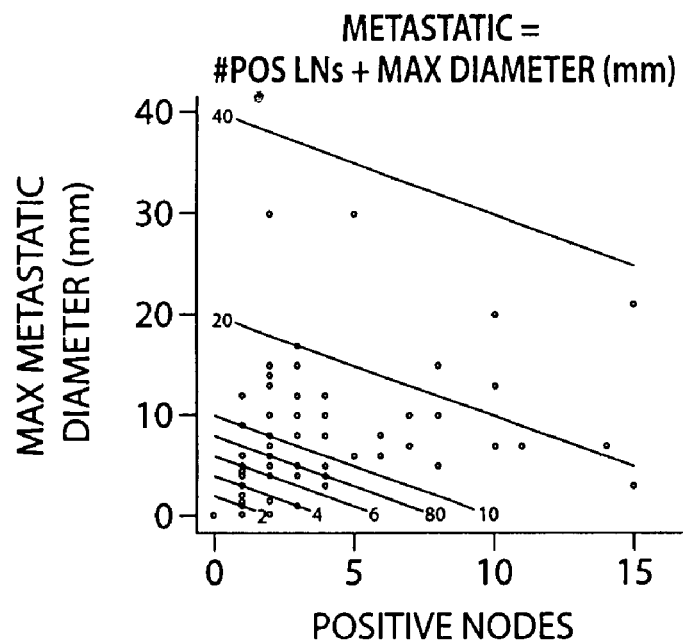
Figure 17D:
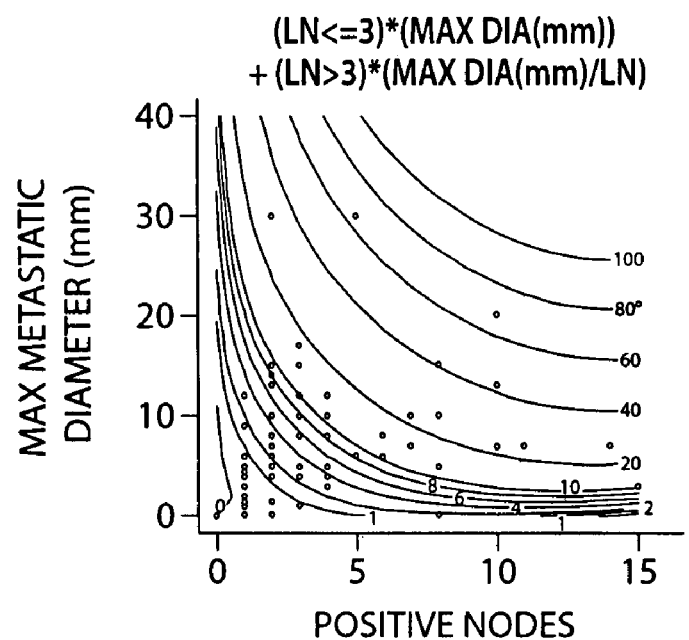
Figure 17E:
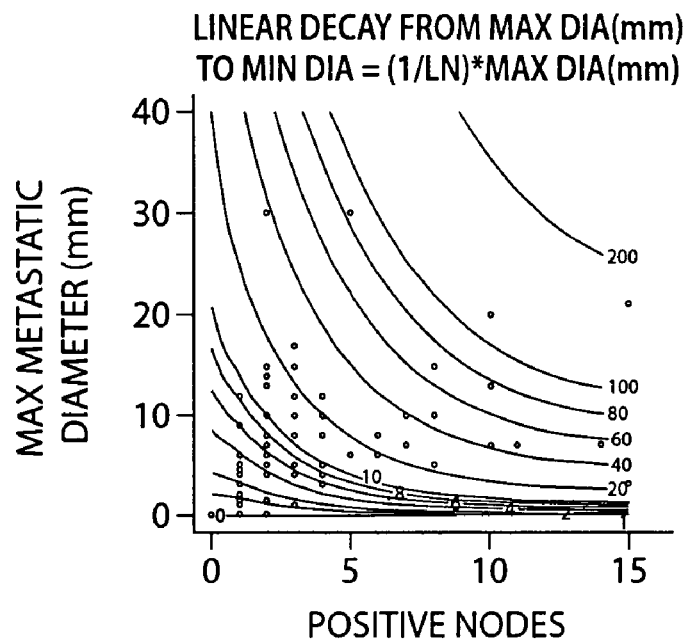
Figure 17F:
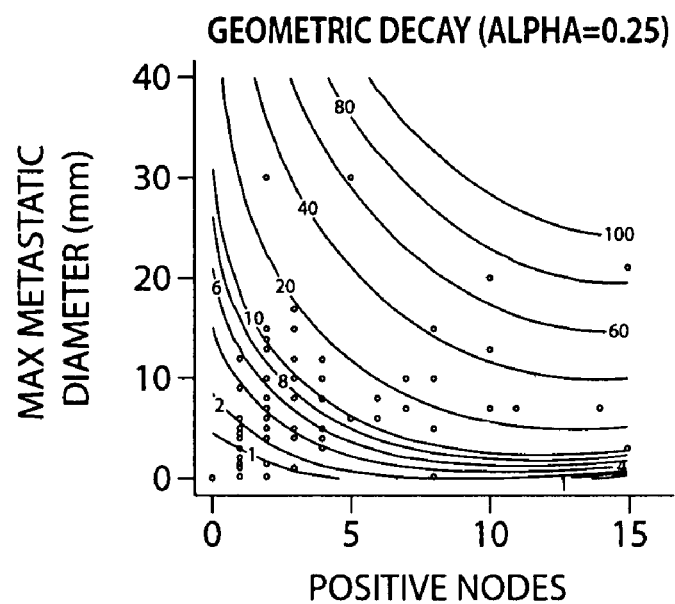

As FIG. 17A shows, the index defined according to Eq. (4) is highly deviant from normality, both for the ER-positive and ER-negative groups, and this would be detrimental to its statistical properties as a potential predictor of survival. To improve the normality of the index, $RCB^{(0)}$ transformed according to an optimal Box-Cox transformation, resulting in the following index that is normally distributed:

$$RCB^{(1)} = [f_{cell}(d_1 d_2) + 0.5(LN)d_{met}^2]^{0.1}. \quad (5)$$

The transformed $RCB^{(1)}$ has more desirable statistical properties as it defines an increasing risk (hazard) with increasing values of RCB and has a uniform 95% confidence interval.

An additional transformation that improves the performance of the index is to use a geometric mean diameter for the primary tumor bed instead of the area and the corresponding diameter of the largest nodal metastasis. The resulting formula is:

$$RCB^{(2)} = [f_{cell}\sqrt{(d_1 d_2)} + 0.5(LN)d_{met}]^{0.1}. \quad (6)$$

2. Definition of Metastatic Contribution to the RCB

The above definition for the metastatic contribution to the RCB implies that all positive lymph nodes contribute as much risk as the largest metastatic node, which overstates the risk of metastatic cancer. Ideally, if the size distribution of the nodes with metastases was available, a more precise definition of this contribution would be possible. However, this is not practical and therefore some assumptions need to be made about the size distribution of the nodal metastases.

Different RCB index definitions will result from different assumptions.

Some representative possibilities and the resulting terms for the metastatic contribution are shown below:

a. All nodes contribute equally to survival risk and proportionately to their area:

$$RCB_{MET}^{(a)} = (LN)d_{met}^2. \quad (7)$$

b. All nodes contribute equally to survival risk and proportionately to their diameter:

$$RCB_{MET}^{(b)} = (LN)d_{met}. \quad (8)$$

c. Number of nodes and node size have additive effects on risk:

$$RCB_{MET}^{(c)} = (LN) + d_{met}(mm), \quad (9)$$

where the maximum nodal metastasis diameter is in mm.

d. The first 3 nodes are treated equivalently, i.e. their diameter is equal to the max diameter.

The remaining nodes have a diameter (1/LN)*(max met diameter):

$$RCB_{MET}^{(d)} = \left[1 + \min(3, LN)\left(\frac{LN-1}{LN}\right)\right]d_{met}. \quad (10)$$

e. Linear decay in the size of metastasis with the number of positive nodes:

$$RCB_{MET}^{(e)} = \left(\frac{1+LN}{2}\right)d_{met}. \quad (11)$$

f. Geometric decay in the size of metastasis with the number of positive nodes (the size decreases by a factor $\alpha$ ($0 < \alpha < 1$):

$$RCB_{MET}^{(f)} = \left[\frac{1-(1-\alpha)^{LN}}{\alpha}\right]d_{met}. \quad (12)$$

FIGS. 17A-F show the "iso-risk" surfaces, i.e. the combinations of number of positive nodes and the size of the largest nodal metastasis that result in the same contributions to the metastatic risk term of the RCB. We see for example that model (a), i.e. the proportional model assuming all nodes contribute the same risk as the largest mode, leads to rather pathologic situations for large values of the two variables that correspond to very large gradients in the risk surface (indicated by high density of contour lines in a region). This means that small changes in one variable will cause very large changes in the risk term, which is not a desirable property. Also it appears that model (c) is too simplistic and does not seem to stratify risk realistically, since one additional positive node contributes to same risk irrespective of the number of positive nodes, and the same is true for the size of the largest metastasis. Model (f) appears to give a well-behaved risk surface with a very gradual increase of risk with the size of the largest metastasis.

3. Scaling and Transformation of the Primary and Metastatic Contributions to RCB Transformations improve the statistical properties of the RCB index irrespective of the specific formulas selected to calculate the primary and metastatic contributions to RCB. Furthermore, in order to have a balanced index, the primary and metastatic contributions need to be scaled to ensure that neither term dominates the index.

Different indices result depending on the order in which normalization and scaling is applied to the two terms:

a) First scale and then transform terms.

Components were first scaled to match the 95$^{th}$ percentile of their corresponding distributions (metastatic term divided by a factor of 3) and then transformed to normality. The resulting formula is:

$$RCB^{(3)} = \left\{f_{cell}\sqrt{(d_1 d_2)} + \left[\frac{1-(1-\alpha)^{LN}}{3\alpha}\right]d_{met}\right\}^{0.2}. \quad (13)$$

This index behaves very well as shown from the Cox proportional hazards analysis of distant relapse free survival.

b) First transform and then scale terms.

Here, the terms are first transformed to normality and then scaled to match the 95$^{th}$ percentiles of their distributions. In this case, the scaling factor was 0.7 for the metastatic term.

The resulting formula is:

$$RCB^{(4)} = (1.4)\left\{f_{cell}\sqrt{(d_1 d_2)}\right\}^{0.17} + \left\{\left[\frac{1-(1-\alpha)^{LN}}{\alpha}\right]d_{met}\right\}^{0.17}. \quad (14)$$

This index behaves better than $RCB^{(3)}$ because it is more sensitive in the high-risk range (large RCB) and it has more uniform 95% confidence interval.

The descriptions given are intended to exemplify, but not limit, the scope of the invention.

REFERENCES

Sataloff D M, Mason B A, Prestipino A J, Seinige U L, Lieber C P, Baloch Z. Pathologic response to induction chemotherapy in locally advanced carcinoma of the breast: a determinant of outcome. J Am Coll Surg 1995; 180:297-304.

Green M C, Buzdar A U, Smith T, Ibrahim N K, Valero V, Rosales M F, et al. Weekly paclitaxel improves pathologic complete remission in operable breast cancer when compared with paclitaxel once every 3 weeks. J Clin Oncol 2005; 23:5983-92.

Feldman L D, Hortobagyi G N, Buzdar A U, Ames F C, Blumenschein G R. Pathological assessment of response to induction chemotherapy in breast cancer. Cancer Res 1986; 46:2578-81.

Altman D G, Royston P. What do we mean by validating a prognostic model? Stat Med 2000; 19:453-73.

Hortobagyi G N, Ames F C, Buzdar A U, Kau S W, McNeese M D, Paulus D, et al. Management of stage III breast cancer with primary chemotherapy, surgery, and radiation therapy. Cancer 1988; 62:2507-16.

Kurosumi M. Significance of histopathological evaluation in primary therapy for breast cancer—recent trends in primary modality with pathological complete response (pCR) as endpoint. Breast Cancer 2004; 11:139-47.

Kattan M W. Judging new markers by their ability to improve predictive accuracy. J Natl Cancer Inst 2003; 95:634-5.

Simon R. Roadmap for developing and validating therapeutically relevant genomic classifiers. J Clin Oncol 2005; 23:7332-41.

Justice A C, Covinsky K E, Berlin J A. Assessing the generalizability of prognostic information. Ann Intern Med 1999; 130:515-24.

Schumacher M, Hollander N, Sauerbrei W. Resampling and cross-validation techniques: a tool to reduce bias caused by model building? Stat Med 1997; 16:2813-27.

Harrell F E, Jr. Regression modelling strategies: with applications to linear models, logistic regression, and survival analysis. New York: Springer-Verlag; 2001.

What is claimed is:

1. A method for predicting relapse risk in a patient undergoing therapy for a solid tumor, the method comprising
providing from a patient with a primary and metastatic tumor $d_1$, $d_2$, $f_{cell}$; LN, and $d_{met}$, wherein
$d_1$ and $d_2$ are bidimensional diameters of a primary tumor bed of said tumor in a resection specimen measured in millimeters;
$f_{cell}$ is the proportion of the primary tumor bed area that contains invasive carcinoma,
LN is the number of regional lymph nodes containing metastatic carcinoma, and
$d_{met}$ is the diameter of the largest metastasis in an regional lymph node,
calculating using a computer a residual cancer burden (RCB) index using said $d_1$, $d_2$, $f_{cell}$, LN and $d_{met}$; and
predicting relapse risk of said patient based on said RCB index, wherein said RCB index is determined using
$RCB=1.4(f_{inv}d_{prim})^{0.17}+[4(1-0.75^{LN})d_{met}]^{0.17}$.

2. The method of claim 1, wherein said patient has multicentric disease.

3. The method of claim 2, wherein said RCB index is calculated using a largest primary tumor bed in said patient.

4. The method of claim 1, further comprising classifying said subject for risk for residual disease based on said RCB index.

5. The method of claim 1, further comprising determining the estrogen receptor (ER) status of said tumor.

6. The method of claim 1, wherein said RCB index is calculated using a computer.

7. The method of claim 1, wherein said RCB index is used to determine the extent of disease in a breast.

8. The method of claim 1, wherein said RCB index is used to determine the extent of disease in the regional lymph nodes.

9. The method of claim 1, wherein said solid tumor is a breast tumor.

10. Software stored in a computer storage medium for predicting survival of a patient undergoing therapy for a solid tumor, the software operable to:
receive for a patient with a primary and metastatic tumor data $d_1$, $d_2$, $f_{cell}$; LN, and $d_{met}$; and
calculate a residual cancer burden (RCB) index using said $d_1$, $d_2$, $f_{cell}$, LN and $d_{met}$ wherein said RCB index is determined using
$RCB=1.4(f_{inv}d_{prim})^{0.17}+[4(1-0.75^{LN})d_{met}]^{0.17}$; and
predict survival of said patient based on said RCB index.

11. The software of claim 10, wherein said solid tumor is a breast tumor.

12. A system for predicting survival of a patient undergoing therapy for a solid tumor, the system comprising
at least one memory operable to store data for $d_1$, $d_2$, $f_{cell}$; LN, and $d_{met}$, for a patient with a primary and metastatic tumor; and
one or more processors, collectively operable to calculate a residual cancer burden (RCB) index using said $d_1$, $d_2$, $f_{cell}$, LN and $d_{met}$,
wherein said RCB index is determined using
$RCB=1.4(f_{inv}d_{prim})^{0.17}+[4(1-0.75^{LN})d_{met}]^{0.17}$.

13. The system of claim 12, wherein said solid tumor is a breast tumor.

14. The method of claim 1, wherein said computer includes software operable to:
receive primary and metastatic tumor data $d_1$, $d_2$, $f_{cell}$; LN, and $d_{met}$, for a patient;
calculate a residual cancer burden (RCB) index using said $d_1$, $d_2$, $f_{cell}$, LN and $d_{met}$; and
predict relapse risk of said patient based on said RCB index.

* * * * *